US011147558B2

(12) United States Patent
Ducic

(10) Patent No.: US 11,147,558 B2
(45) Date of Patent: Oct. 19, 2021

(54) MATERIALS AND METHODS FOR NERVE REPAIR WITH ANIMAL-SOURCED GRAFTS

(71) Applicant: AxoGen Corporation, Alachua, FL (US)

(72) Inventor: Ivica Ducic, Alachua, FL (US)

(73) Assignee: Axogen Corporation, Alachua, FL (US)

( * ) Notice: Subject to any disclaimer, the term of this patent is extended or adjusted under 35 U.S.C. 154(b) by 124 days.

(21) Appl. No.: 16/192,261

(22) Filed: Nov. 15, 2018

(65) Prior Publication Data

US 2020/0155156 A1  May 21, 2020

(51) Int. Cl.
 *A61B 17/11* (2006.01)
 *A61L 27/36* (2006.01)
 *A61B 17/00* (2006.01)

(52) U.S. Cl.
 CPC ...... *A61B 17/1128* (2013.01); *A61L 27/3604* (2013.01); *A61L 27/3675* (2013.01); *A61B 2017/00796* (2013.01); *A61B 2017/00969* (2013.01); *A61L 2430/32* (2013.01)

(58) Field of Classification Search
 CPC .............. A61B 17/1128; A61B 2/12; A61B 2017/00796; A61B 2017/00969; A61L 27/3604; A61L 27/3675
 See application file for complete search history.

(56) References Cited

U.S. PATENT DOCUMENTS

| 4,662,884 | A | * | 5/1987 | Stensaas | A61B 17/1128 606/152 |
|---|---|---|---|---|---|
| 6,235,041 | B1 | | 5/2001 | Cheng et al. | |
| 10,813,643 | B2 | * | 10/2020 | Ducic | A61B 17/1128 |
| 2001/0017138 | A1 | * | 8/2001 | Cheng | A61B 17/1128 128/898 |
| 2003/0040112 | A1 | * | 2/2003 | Muir | A61K 35/30 435/368 |
| 2011/0129515 | A1 | | 6/2011 | Archibald | |
| 2012/0059399 | A1 | * | 3/2012 | Hoke | A61B 17/00491 606/153 |

(Continued)

OTHER PUBLICATIONS

Wang, Y. et al., "How to Measure Outcomes of Peripheral Nerve Surgery." Hand Clin., Aug. 2013, 29 (3): 349-361.

(Continued)

*Primary Examiner* — Alexander J Orkin
(74) *Attorney, Agent, or Firm* — Bookoff McAndrews, PLLC

(57) ABSTRACT

The subject invention pertains to materials, including sets of nerve grafts, for performing breast neurotization with xenograft nerves in breast surgeries, such as reconstructive breast surgery. Certain embodiments of the set of nerve grafts comprise at least two nerve grafts prepared from one or more nerves, such as one or more intercostal nerves (ICNs), obtained from one or more animal sources. Such animal-sourced nerve grafts may be used as xenografts in the reconstruction of nerve defects in humans, and in particular, animal-sourced ICN grafts may be used as xenografts in the reconstruction of ICN nerve defects in humans, including through use of the breast neurotization technique described herein. These animal-sourced nerve grafts may also be used in the reconstruction of nerve defects in animal recipients, including as xenografts, allografts and autografts.

19 Claims, 20 Drawing Sheets

(56) References Cited

U.S. PATENT DOCUMENTS

| | | | |
|---|---|---|---|
| 2016/0074042 A1 | 3/2016 | Vogt et al. | |
| 2017/0354759 A1 | 12/2017 | Xu et al. | |
| 2018/0140434 A1 | 5/2018 | Frostell et al. | |
| 2018/0140742 A1 | 5/2018 | Uchida et al. | |
| 2019/0008903 A1 | 1/2019 | Huang et al. | |
| 2019/0029686 A1 | 1/2019 | Agarwal et al. | |
| 2019/0046692 A1 | 2/2019 | Shefi et al. | |
| 2019/0117227 A1* | 4/2019 | Ducic ................ | A61B 17/1128 |
| 2019/0175788 A1 | 6/2019 | Brown et al. | |
| 2019/0217089 A1 | 7/2019 | Bayat et al. | |
| 2019/0247511 A1 | 8/2019 | Tomlinson et al. | |
| 2019/0262500 A1 | 8/2019 | Xu et al. | |

OTHER PUBLICATIONS

Whitlock, E. L. et al., "Processed allografts and type I collagen for repair of peripheral nerve gaps." Muscle Nerve, Jun. 2009, 39 (6): Abstract.

Wolford, L. M., Rodrigues, D. B., "Autogenous grafts/allografts. conduits for bridging peripheral trigeminal nerve gaps" Atlas Oral Maxillofac. Surg. Clin. North Am., Mar. 2011, 19 (1): Abstract.

Yan, S., "An early history of human breast cancer: West meets East." Chinese Journal of Cancer, 2013, 32 (9): 475-477.

International Search Report and Written Opinion issued in counterpart International Application Serial No. PCT/US18/056734 dated Dec. 26, 2018.

Puonti, Helena, Effects of Microsugical Nerve Repair On Sensory Function After Breast Reconstruction: Jan. 27, 2017; p. 71; URL: <https://helda.helsinki.fi/bitstream/handle/10138/173219/Effectso. pdf? sequence_1&isAllowed=y>.

Spiegel, A. et al., Breast Reinnervation: DIEP Neurotization Using the Third Anterior Ntercostal Nerve: Plastic Reconstruction Surgery Global Open: vol. 1. Nov. 2013; entire document.

Yueh, J. H. et al., "Patient Satisfaction in Postmastectomy Breast Reconstruction: A Comparative Evaluation of DIEP, TRAM, Latissimus Flap, and Implant Techniques." Plastic and Reconstructive Suegery, Jun. 2010, 125 (6): 1585-1595.

Zhong, T. et al., "High-frequency ultrasound: a useful tool for evaluating the abdominal wall following free TRAM and DIEP flap surgery." Plastic and Reconstructive Surgery, 117 (4): Abstract.

Zuniga, J. R., "Sensory Outcomes After Reconstruction of Lingual and Inferior Alveolar Nerve Discontinuities Using Processed Nerve Allograft—A case Series." J. Oral Maxillofac. Surg., 2015, 73:734-744.

Zurrida, S., Umberto, V., "Milestones in Breast Cancer Treatment." The Breast Journal, 2015, 21 (1): 3-12.

Allen, R. J., "DIEP Versus TRAM for Breast Reconstruction." Plastic and Reconstructive Surgery, Jun. 2003, 111 (7): Abstract.

Beugels, J. et al., "Sensory recovery of the breast after innervated and non-innervated autologous breast reconstructions: A systematic review." J. Plast. Reconstr. Aesthet. Surg., Sep. 2017, 70 (9): Abstract.

Blondeel, P. N. et al., "Sensory nerve repair in perforator flaps for autologous breast reconstruction: sensational of senseless?" British Journal of Plastic Surgery, 1999, 52: 37-44.

Blondeel, P. N. et al., "The donor site morbidity of free DIEP flaps and free TRAM flaps for breast reconstruction." British Journal of Plastic Surgery, 1997, 50: 322-330.

Boeckstyns, M. E. et al. "Collagen conduit versus microsurgical neurorrhaphy: 2-year follow-up of a prospective, blinded clinical and electrophysiological multicenter randomized, controlled trial." J. Hand. Surg. Am. Dec. 2013, 38 (12): Abstract.

Brooks, D. N. et al., "Processed Nerve Allografts for Preipheral Nerve Reconstruction: A Multicenter Study of Utilization and Outcomes in Sensory, Mixed, and Motor Nerve Reconstruction." Microsurgery, 2011, 1-14.

Chen, C. M. et al., "Immediate Postoperative Complications in DIEP versus Free/Muscle-Sparing TRAM Flaps." Plastic and Reconstructive Surgery, Nov. 2007, 120 (6): 1477-1482.

Ducic, I. et al. "Chronic postoperative breast pain: danger zones for nerve injuries." Plast. Reconstr. Surg., Jan. 2011, 127 (1): Abstract.

Ducic, I. et al. "Innovative Treatment of Peripheral Nerve Injuries." Peripheral Nerve Surgery & Research, Feb. 2012, 68 (2): 180-187.

Ducic, I. et al., "Nerve Injuries in Aesthetic Breast Surgery: Systematic Review and Treatment Options." Aesthetic Surgery Journal, Mar. 2014, 34 (6): 841-856.

Ducic, I., Larson, E. E., "Outcomes of surgical treatment for chronic postoperative breast and abdominal pain attributed to the intercostal nerve " J. Am. Coll. Surg., Sep. 2006, 203(3): Abstract.

Ducic, I., et al., "Refinements of nerve repair with connector-assisted coaptation." Microsurgery, Mar. 2017, 37 (3): Abstract.

Enajat, M. et al., "Thermal injuries in the insensate deep inferior epigastric artery perforator flap: case series and literature review on mechanism of injury." Microsurgery, 2009, 29 (3): Abstract.

Guo, Y. et al., "Sensory recovery following decellularized nerve allograft transplantation for digital nerve repair." J. Plast. Surg. Hand Surg., Dec. 2013, 47 (6): Abstract.

Ijpma, F. F. et al., "Sural nerve donor-site morbidity: thirty-four years of follow-up." Ann. Plast. Surg., Oct. 2006, 57 (4): Abstract.

Kay, A. R., "Susceptibility of the Insensate Reconstructed Breast to Burn Injury." Plastic and Reconstructive Surgery, Mar. 1997, 99 (3): 927.

Knox, A. D. et al., "Comparison of Outcomes following Autologous Breast Reconstruction Using the DIEP and Pedicled TRAM Flaps: A 12-Year Clinical Retrospective Study and Literature Review." Plast. Reconstr. Surg., Jul. 2016, 138(1): Abstract.

Lehmann, C. et al., "Sensibility and cutaneous reinnervation after breast reconstruction with musculocutaneous flaps." Ann. Plast. Surg., Apr. 1991, 26 (4): Abstract.

Liew, S. et al., "Sensory recovery following free TRAM flap breast reconstruction." British Journal of Plastic Surgery, 1996, 49: 210-213.

Lohmeyer, J. A. et al., "Prospective clinical study of digital nerve repair with collagen nerve conduits and review of literature." J. Reconstr. Microsurg., May 2014, 30 (4): Abstract.

Lundborg, G., "A 25-year perspective of peripheral nerve surgery: evolving neroscientific concepts and clinical significance." J. Hand Surg. Am., May 2000, 25 (3): Abstract.

Mackinnon, S. E., Dellon, A. L., "A study of nerve regeneration across synthetic (Maxon) and biologic (collagen) nerve conduits for nerve gaps up to 5 cm in the primate" J. Reconstr. Microsurg., Apr. 1990, 6(2): Abstract.

Mahajan, A. L. et al., "Sun Bum as a consequence of resting reading glasses on a reconstructed breast." J Plast. Reconstr. Aesthet. Surg., Feb. 2010, 63 (2): Abstract.

Means K. R. Jr. et al., "A Multicenter, Prospective, Randomized, Pilot Study of Outcomes for Digital Nerve Repair in the Hand Using Hollow Conduit Compared with Processed Allograft Nerve." HAND, 2016, 11 (2): 144-151.

Meek, M. F. et al., "Poor results after nerve grafting in the upper extremity: Quo vadis?" Microsurgery, 2005, 25 (5): Abstract.

Mennie, J. C. et al., "Donor-Site Hernia Repair in Abdominal Flap Breast Reconstruction: A Population-Based Cohort Study of 7929 Patients." Plast. Reconstr. Surg., Jul. 2015, 136 (1): Abstract.

Moore, A. M. et al., "Principles of Nerve Repair in Complex Mounds of the Upper Extremity." Semin. Plast. Surg., 2015, 29: 40-47.

Nahabedian, M. Y. et al., "Breast Reconstruction with the DIEP Flap or the Muscle-Sparing (MS-2) Free TRAM Flap: in There a Difference?" Plastic and Reconstructive Surgery, Feb. 2005, 15(2): 436-444.

Nahabedian, M. Y. et al., "Breast Reconstruction with the Free TRAM of DIEP Flap: Patient Selection, Choice of Flap, and Outcome." Plastic and Reconstructive Surgery, Aug. 2002, 110 (2): 466-475.

Nahabedian, M. Y., Mcgibbon, B. M., "Thermal injuries in autogenous tissue breast reconstruction." British Journal of Plastic Surgery, 1998, 51: 599-602.

Place, M. J. et al., "Sensory reinnervation of autologous tissue TRAM flaps after breast reconstruction." Ann. Plast. Surg., Jan. 1997, 38 (1): Abstract.

(56) References Cited

OTHER PUBLICATIONS

Pusic, A. L. et al., "Development of a new patient-reported outcome measure for breast surgery: the BREAST-Q." Plast. Reconstr. Surg., Aug. 2009, 12 (2): Abstract.

Rabin, R. C., "After Mastectomies, an Unexpected Blow: Numb New Breasts." The New York Times, Jan. 29, 2017, Retrieved from Internet: <http://www.nytimes.com/2017/01/29/well/live/after-mastectomies-an-unexpected-blow-numb-new-breasts.html>.

Rinker, B. D. et al., "Outcomes of short-gap sensory nerve injuries reconstructed with processed nerve allografts from a multicenter registry study" J. Reconstr. Microsurg., Jun. 2015, 31 (5): Abstract.

Rosen, B., Lundborg, G., "A model instrument for the documentation of outcome after nerve repair." J. Hand Surg. Am., May 2000, 25 (3): Abstract.

Rozen, W. M. et al., "Avoiding Denervation of Rectus Abdominis in DIEP Flap Harvest: the Importance of Medical Row Perforators" Plastic and Reconstructive Surgery, Sep. 2008, 122 (3): 710-716.

Safa. B., Buncke, G., "Autograft Substitutes: Conduits and Processed Nerve Allografts." Hand Clin., May 2016, 32 (2): Abstract.

Santanelli, F. et al., "Prospective computerized analyses of sensibility in breast reconstruction with nonreinnervated DIEP flap." Plastic and Reconstructive Surgery, May 2011, 127 (5): Abstract.

Sarhadi, N. S. et al., An anatomical study of the nerve supply of the breast, including the nipple and areola. British Journal of Plastic Surgery, 1996, 49: 156-164.

Schlenz, I. et al., "The Sensitivity of the Nipple-Areola Complex: An Anatomic Study." Plastic and Reconstructive Surgery, Mar. 2000, 105 (3): 905-909.

Shaw, W. W. et al., "The spontaneous return of sensibility in breasts reconstructed with autologous tissues." Plast. Reconstr. Surg., Feb. 1997, 99 (2): Abstract.

Spiegel, A. J. et al., "Breast Reinnervation: DIEP Neurotization Using the Third anterior Intercostal Nerve." PRS GO, 2013, 1-9.

Stromps, J. P. et al., "Spontaneous Reinnervation of Deep Inferior Epigastic Perforator Flaps after Delayed Breast Reconstruction." J. Reconstr. Microsurg., Mar. 2016, 32 (3): Abstract.

Temple, C. L. et al., "Sensibility following innervated free TRAM flap for breast reconstruction." Plast. Reconstr. Surg., Jun. 2006, 117 (7): Abstract.

Temple, C. L. et al., "Sensibility following innervated free TRAM flap for breast reconstruction: Part II. Innervation improves patient-rated quality of life" Plastic and Reconstructive Surgery, Nov. 2009, 124 (5): Abstract.

Tindholdt, T. T., Tonseih, K. A., "Spontaneous reinnervation of deep inferior epigastric artery perforator flaps after secondary breast reconstruction." Scand. J. Plast. Reconstr. Surg. Hand Surg., 2008, 42 (1): Abstract.

* cited by examiner

MATERIALS AND METHODS FOR NERVE REPAIR WITH ANIMAL-SOURCED GRAFTS

BACKGROUND OF THE INVENTION

First descriptions of breast cancer can be found in the early medical writings of the ancient Greeks and Egyptians that date back to 480 B.C. However, modern treatment did not start until Halsted performed the first mastectomy in the 1880s. Since then, understanding and treatment of breast cancer has evolved significantly. Today, post-mastectomy breast reconstruction is a fundamental element in breast cancer care. Although implant-based breast reconstruction is today's more common reconstructive modality, long-term patient satisfaction is reportedly higher following autologous reconstruction. Hence, it is not surprising that many patients choose this reconstructive modality. Despite significant technical advances that have been made in autologous reconstruction, such as the development of perforator-based flaps that minimize donor-site morbidity, abdominal wall weakness and donor-site hernias remain significant complications.

Interestingly, the abundance of reports that focus on donor-site morbidity is contrasted by the paucity of studies focusing on recipient-site outcomes beyond just flap survival. The importance of breast sensation cannot be overstated as it has a tremendous impact on postoperative quality of life. In fact, the issue of post-mastectomy loss of sensation has recently been prominently addressed even in the mainstream media. Hence, patients are increasingly inquiring about modalities that not only reconstruct the breast but also restore sensation. A topic of much debate in this regard is breast neurotization by virtue of flap reinnervation/neurotization at the time of transfer.

Breast neurotization is not a novel topic and has been discussed in the literature since the early 1990s. Yet, since the introduction of sensate flaps for breast reconstruction, the debate has centered upon whether nerve coaptation is necessary for recovery of flap sensation or is collateral ingrowth of the nerve fibers sufficient for meaningful sensation. Available evidence suggests that restoration of sensation is important. Cases of involuntary thermal and mechanical injuries have been reported with a resultant negative impact on patient-rated quality of life metrics. Multiple studies have shown that breast neurotization of the donor flap nerves has resulted in more expeditious and improved sensory recovery, improved patient satisfaction, and patient-reported quality of life. On the other hand, several studies have failed to demonstrate such a difference in outcomes. An additional point of debate has been whether the achievable outcomes following nerve coaptation justify the additional operative time. Spontaneous reinnervation does occur to varying extents, but that sensory recovery of innervated flaps is superior, starts earlier, and gradually improves over time with a higher chance of approaching normal sensation compared to non-innervated flaps.

Notably, high heterogeneity and lack of standardization exist between the studies, which prevents a meta-analysis of breast surgery outcomes. A specific area of concern is the lack of standardization of the neurotization procedure itself, varying from primary nerve repair to the use of nerve conduits. Spiegel et al. evaluated sensory recovery of autologous flaps and compared the use of a nerve conduit and direct nerve coaptation to controls, i.e. spontaneous reinnervation. They concluded that flap neurotization was superior to spontaneous innervation, that the neurotization procedure did not prolong operative time significantly, and that the use of a nerve conduit improved sensory recovery significantly over direct coaptation.

In certain conventional surgeries, return of sensation was observed, but for conduit neurotized flaps the return of sensation was noted to be only half of that of the contralateral non-operated breast skin and for direct coaptation, the flap required four times higher pressure to reach sensibility. Although, there was return of sensation, meaningful sensory recovery following breast reconstruction is still desired.

One of the commonly used metrics to evaluate sensory outcome after peripheral nerve surgery is the Medical Research Council (MRC) scale. The scale runs from S0 to S4 where S0 is no sensory recovery, S1 is recovery of deep cutaneous pain, S2 is return of some superficial cutaneous pain and some degree of tactile sensibility, S3 is return of superficial cutaneous pain and tactile sensibility without over response, S3+ is return of superficial cutaneous pain and tactile sensibility with some 2-point discrimination recovery, and S4 is complete sensory recovery. The scale has been used to measure meaningful recovery which in some studies has been a defined as S3 and above. Secondly, it was noted that neurotization only required 10 to 15 additional minutes of operative time. However, given the prior concerns of an insensate flap, the opportunity to restore sensation to the reconstructed breast should outweigh concerns related to potential case prolongation. Lastly, they state that the nerve conduit used was a 40 mm nerve conduit. Lohmeyer et al. (2014, *J Reconstr Microsurg.*; 30(4):227-34) performed a literature review for sensibility after digital nerve reconstructions with nerve conduits of varying lengths. They measured 2-point-discrimination and monofilament testing following reconstruction with nerve conduits between 5 to 25 mm and found that sensibility began to diminish after a conduit gap length of 6 mm. Monofilament testing was significantly worse after 12 mm, poor sensibility was noted after 15 mm, and over 20% of the patients in their review regained no sensibility. In light of these kind of reviews, the use of tube conduits for breast neurotization or any other nerve surgery with gaps larger than 6 mm is not advisable.

Breast neurotization is typically performed with autograft harvest. Autograft harvest involves harvesting autogenous nerves from abdominal sites and implanting the nerves into the recipient patient's breast tissue. Autograft harvest based breast neurotization requires longer operation room procedures and increased risk of muscle denervation. Muscle denervation causes laxity, loss of muscle tone, poor aesthetic outcome, and increased risk of incisional hernia. Autograft harvest also involves loss of regenerative capacity because half of nerve diameter goes to muscle and produces dead ends. Therefore, surgical methods that avoid problems associated with autograft harvest based breast neurotization are desirable.

BRIEF SUMMARY OF THE INVENTION

To overcome these shortcomings, the invention provides a standardized and reproducible surgical procedures, and related materials, that allow for conservation of the innervation to the rectus abdominis while allowing for neurotization of the flap. In certain embodiments, the nerve allograft is used as a novel bridging material in breast neurotization, which overcomes shortcomings of direct coaptation, conduit, or autograft applications, and reflects on connector-assisted nerve coaptation facilitating the nerve repair.

The subject invention provides materials and methods for performing breast neurotization with nerve grafts in breast surgeries, such as reconstructive breast surgery. The methods of the invention mitigate risks of conventional surgical methods and provide alternative approaches and mitigation plans.

DETAILED DESCRIPTION OF THE INVENTION

Figure 1:
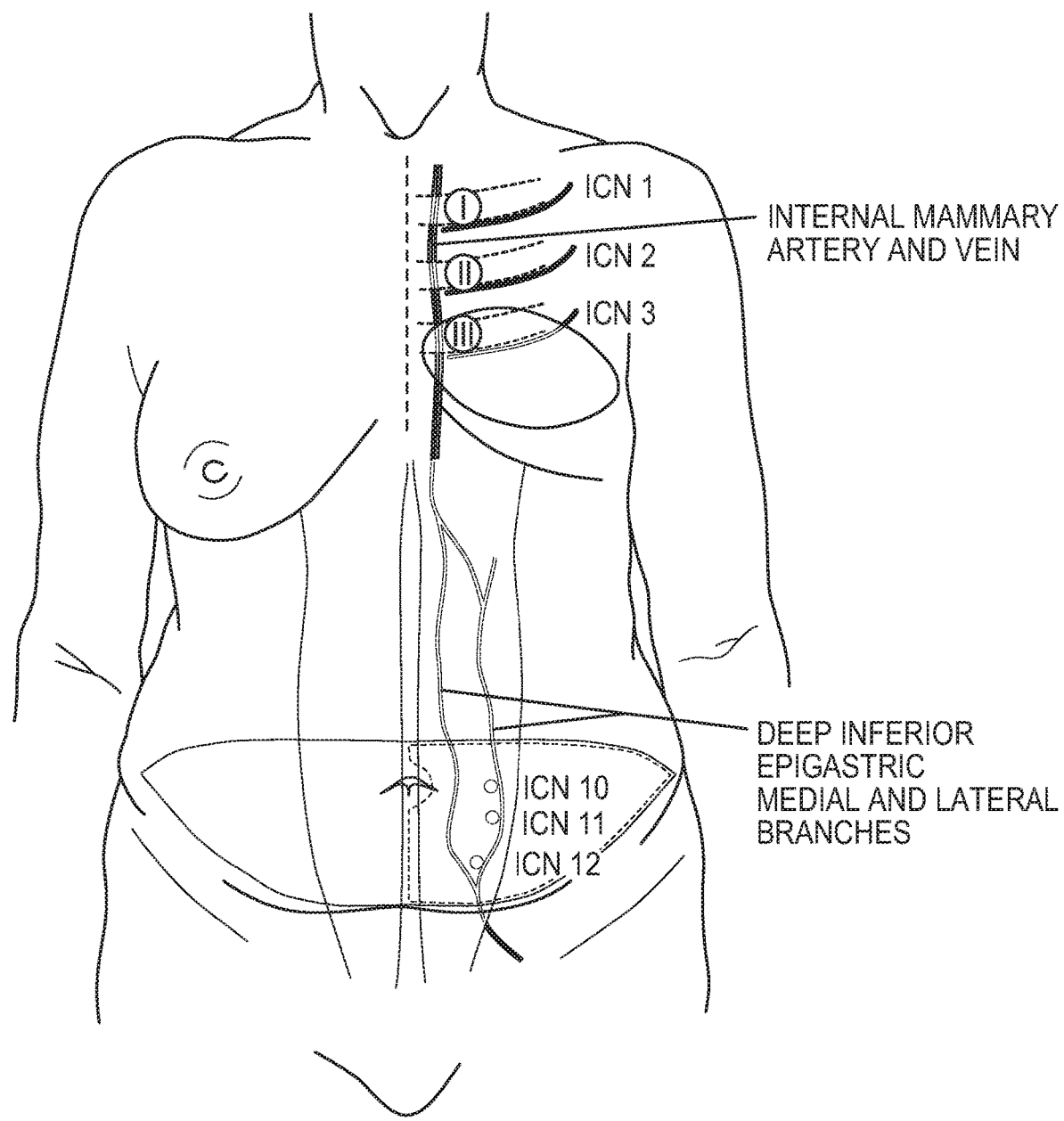
FIG. 1 shows key anatomical landmarks for DIEP flap breast neurotization. Outlines of DIEP abdominal flap and post-mastectomy chest wall defect. Essential nerves (ICN1, ICN2, ICN3, ICN10, ICN11, ICN12), vascular structures (medial and lateral DIEA, internal mammary artery and vein), and bony landmarks (ribs I, II, III) are shown.

The invention provides surgical methods for implanting autogenous or allogeneic nerves into a patient's breast. Such implantation induces breast neurotization of the breast tissue in the patient that has undergone or is undergoing a breast surgery, such as mastectomy or breast reconstruction surgery.

In preferred embodiments, the methods provided herein allow for neurotization of the entire breast tissue flap via an autogenous or allogeneic nerve graft. The methods comprise implanting nerve tubes, including synthetic nerve tubes, allogeneic nerves, or autogenous nerves into breast flap.

Deep inferior epigastric perforator (DIEP) flap breast reconstructions have been known to have limited return of sensation at the recipient site, and potentially cause abdominal bulge and wall weakness at the donor site. Breast neurotization or reinnervation of reconstructed breast flaps have been shown to have protective effects against mechanical or thermal injuries as well as positive effects on a patient's quality of life. However, simultaneous breast neurotization of the flap area is yet to be a standardized component in breast reconstruction procedures after mastectomies. In addition, current clinical breast neurotization data point to the lack of a standardized operative approach, a standard nerve gap bridging medium, and a paucity in homogenous data for clinical sensory recovery outcomes.

With these issues in mind, certain embodiments of the invention provide surgical techniques that minimize abdominal wall morbidities, provide a standardized breast neurotization technique, and increase the chances of meaningful sensory recovery by utilizing the human processed nerve allograft as the preferred nerve gap bridging material. This operative technique is unique in the use of the nerve allograft for breast neurotization and selective use of only the sensory component of the flap, while preserving the rectus abdominis motor innervation.

Processed nerve allografts have been shown in clinical studies to be effective in bridging gap lengths up to 70 mm, with superior meaningful sensory recovery outcomes compared to hollow tube nerve conduits, and comparable to nerve autografts without the additional operative morbidities. The surgical methods of the invention can be customized to enable single or dual nerve breast neurotization and this novel approach performs favorably compared to conduit or autograft neurotization. The materials and methods of the subject invention enable surgeons to apply a standardized and reproducible breast neurotization surgery, further optimizing chances of meaningful sensory recovery.

Breast neurotization is an important component of breast reconstruction. The invention demonstrates the importance of taking only the sensory branch and preserving the motor branch at the donor site. This selectivity prevents aberrant nerve regeneration of the recipient sensory nerve into a blind motor stump thus optimizing sensory outcomes. This also provides anatomical justification for why sensation recovery in the autograft-neurotized breasts is less than expected.

Further, the technical aspect in selectively dissecting and extracting only the sensory components of ICN11 and/or ICN12 along with the selective use of medial row perforators minimizes the risk of rectus abdominis denervation and the associated morbidities.

The identification and utilization of reliable predictable landmarks allows the surgical methods of the invention to be consistently repeated.

Hollow tube nerve conduits alone are not suitable for breast neurotization and the human processed nerve allograft based on non-breast neurotization studies would be the ideal and most promising bridging medium. In addition, allograft nerve reconstructions compare favorably to nerve autograft outcomes but without the additional donor site associated morbidities. Thus, nerve allografts are a vital element for this technique.

Lastly, the utilization of the connector-assisted nerve coaptation eliminates misalignment risks. By incorporating the processed nerve allograft in the surgical methods, the invention provides standardized breast neurotization during breast reconstruction, minimized abdominal wall related morbidities, and improved meaningful sensory recovery and thus quality of life in breast reconstruction patients.

In certain embodiments, the invention provides a surgical method for breast neurotization. The method comprises implanting an allogeneic or autologous nerve to the patient's breast flap. In some embodiments, the allogeneic or autologous nerve is obtained from an intercostal nerve (ICN), particularly, ICN10, ICN11, or ICN12.

In a single allograft, an allogeneic or autologous ICN10, ICN11, or ICN12 is harvested and implanted to the patient's ICN2 or ICN3. For example, an allogeneic or autologous nerve from ICN10, ICN11, and ICN12 is harvested and implanted to one of the patient's ICN2 or ICN3. For example, ICN10 or ICN11 can be harvested and implanted to ICN2 or ICN3. Alternatively, ICN11 or ICN12 can be harvested and implanted to ICN2 or ICN3. Certain such embodiments are described in FIGS. 12 and 13.

In a dual graft, two nerves from ICN10, ICN11, or ICN12 are harvested and implanted to the patient's ICN2 and ICN3. For example, two nerves from ICN10, ICN11, and ICN12 are harvested and each is implanted to one of the patient's ICN2 and ICN3. Alternatively, ICN10 and ICN11 can be harvested and implanted to ICN2 and ICN3, respectively. Similarly, ICN11 and ICN12 can be harvested and implanted to ICN2 and ICN3, respectively. Certain such embodiments are described in FIGS. 12 and 13.

In certain embodiments, only the sensory portion of the nerve ICN10, ICN11, or ICN12 is harvested and implanted in the sensory portion of the nerve ICN2 or ICN3. In certain such embodiments, only the sensory portions of two of the nerves ICN10, ICN11, and ICN12 are harvested and each is implanted in the sensory portion of the nerve ICN2 or ICN3.

Harvesting only the sensory portions of the nerves from ICN10, ICN11, or ICN12 retains the motor innervation in the rectus abdominis. By conserving the motor component of the lateral intercostal nerves to the lateral rectus, abdominal wall morbidity is minimized.

In further embodiments, processed nerve allograft is used as the bridging material in implantation of the donor nerve. Alternatively, nerve tubes can be used as the bridging material in the implantation of the donor nerve.

The nerve tubes or processed nerve allografts used in certain embodiments of the invention can contain neurotrophic growth factors that stimulate nerve regeneration. Inclusion of such growth factors facilitates innervation of the flap tissue. Such growth factors include brain-derived neurotrophic factor (BDNF), glial cell-derived neurotrophic factor (GDNF), neurotrophic factor (NGF), neutrophin-3 (NT-3), ciliary neurotrophic factor (CNTF), and leukemia inhibitory factor (LIF).

Certain examples of nerve regeneration tubes are described in the U.S. Pat. Nos. 9,687,592; 9,108,042; 9,017,714; 8,741,328; 8,632,844; 8,603,512; 7,842,304; 7,615,063; 7,135,040; 6,589,257; 6,090,117; 5,656,605; and 4,778,467. Each of these patents is incorporated herein by reference in its entirety.

Further embodiments of the invention provide a set of nerve grafts comprising at least two nerve grafts prepared from ICN10, ICN11, and ICN12. In some embodiments the set comprises at least two nerve grafts are prepared from ICN10, ICN11, and ICN12 obtained from one donor. In other embodiments, the set comprises at least two nerve grafts prepared from ICN10, ICN11, and ICN12 obtained from different donors. A set of nerve grafts disclosed herein can be used in a suitable surgery, for example, breast neurotization surgery described herein.

In some embodiments, a set of nerve grafts may be prepared from one or more intercostal nerves that are obtained from one or more animal sources. Examples of animal sources may generally include non-ruminants in addition to ruminants such as, but not limited to, sheep, cows, horses, pigs, goats, etc. It will be appreciated that other animals may be sources of a set of nerve grafts for use in humans or animals, as appropriate. It will also be appreciated that nerve grafts prepared from one or more intercostal nerves obtained from one or more animal sources may be used in surgical techniques akin to those described herein. For example, one of ordinary skill in the art will recognize that variations on the surgical techniques described herein may be utilized depending on the graft source (e.g., human, animal, etc.) and on the graft recipient (e.g., human, animal, etc.). It will also be appreciated that such animal-sourced grafts may be used as xenografts in the breast neurotization techniques described herein in humans, or may be used (as xenografts, allografts or autografts) in reconstruction of intercostal nerve defects in animals. In some implementations, the at least two nerve grafts may be prepared from at least two different ICNs obtained from a single animal source. A single animal source may comprise a single animal (e.g., one sheep) or multiple animals (e.g., multiple sheep). In some implementations, the at least two nerve grafts may be prepared from at least two different ICNs obtained from different animal sources. Different animal sources may comprise multiple different animals (e.g., a sheep and a pig, or two different species of sheep).

In yet additional embodiments, a set of nerve grafts may be prepared from one or more nerves that are obtained from one or more animal sources, including from those animal sources described above. Such grafts may be used as xenografts in the reconstruction of nerve defects in humans, or may be used as xenografts, allografts or autografts in the reconstruction of nerve defects in animals.

Each of the nerve grafts in the set of nerve grafts of the invention can be processed to prepare nerve grafts suitable for implantation in a recipient. Certain techniques of processing nerves to produce nerve grafts are described in U.S. Pat. Nos. 9,572,911; 9,402,868; 7,851,447; and 6,972,168. Each of these patents is incorporated herein by reference in its entirety.

Definitions

An autologous graft is an organ, a tissue, or a part thereof obtained from a first site from a subject for implantation to a second site in the subject.

An allogeneic graft is an organ, a tissue, or a part thereof obtained from a first individual for implantation to a second individual of the same species as the first individual.

Neurotization refers to re-innervation of nerves in a portion of a body that has lost its innervation through irreparable damage to its nerve. Neurotization does not require a complete return of the sensation, sensory, or motor properties of the portion of the body that lost its innervation.

Example 1—Surgical Methods of the Invention

Figure 2A:
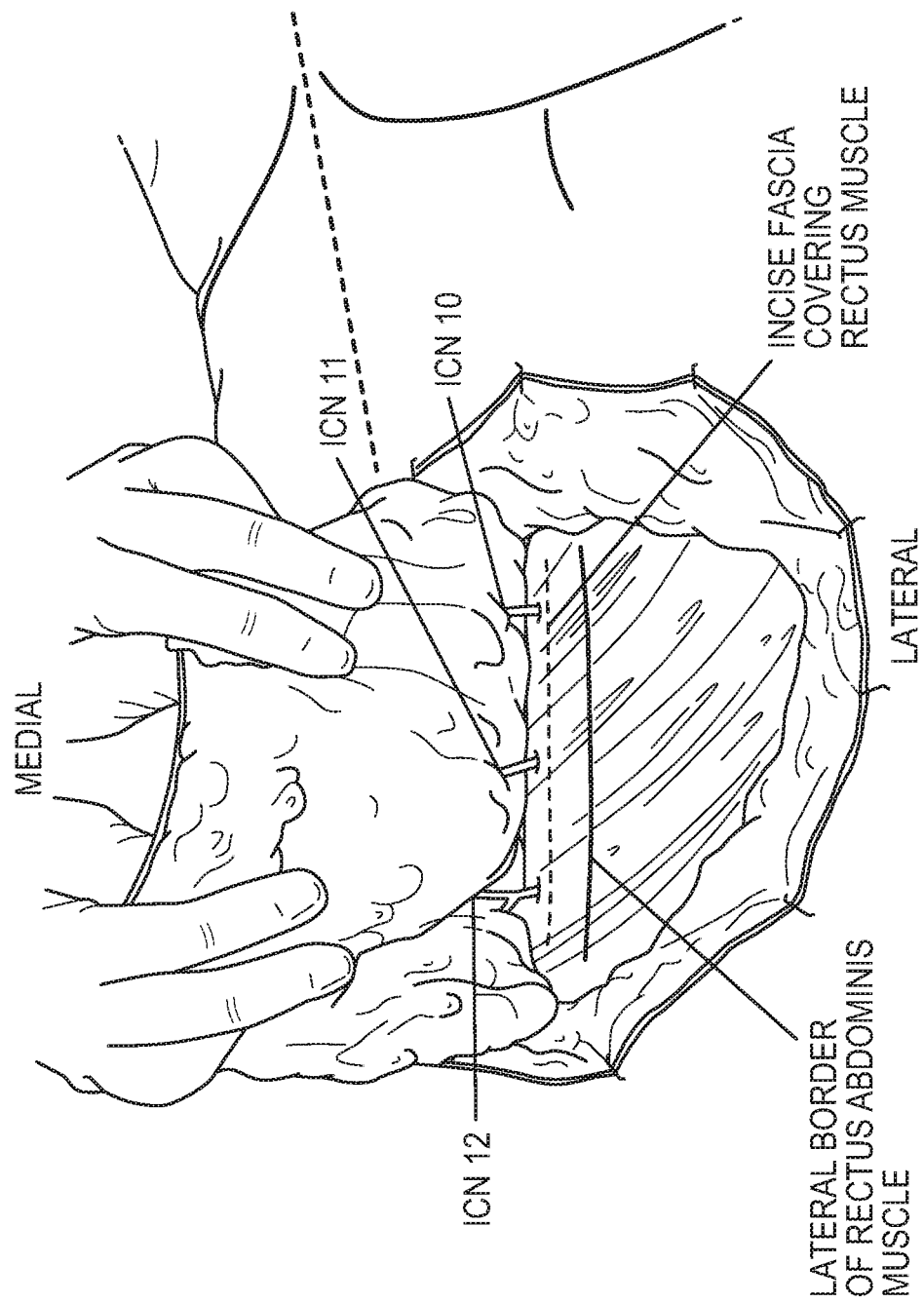
FIG. 2A shows DIEP flap dissection in standard lateral to medial fashion. Schematic demonstrating typical positions of distal ends of the sensory components of respective intercostal nerves and expected incision of rectus sheath lateral to intercostal nerves.
Figure 2B:
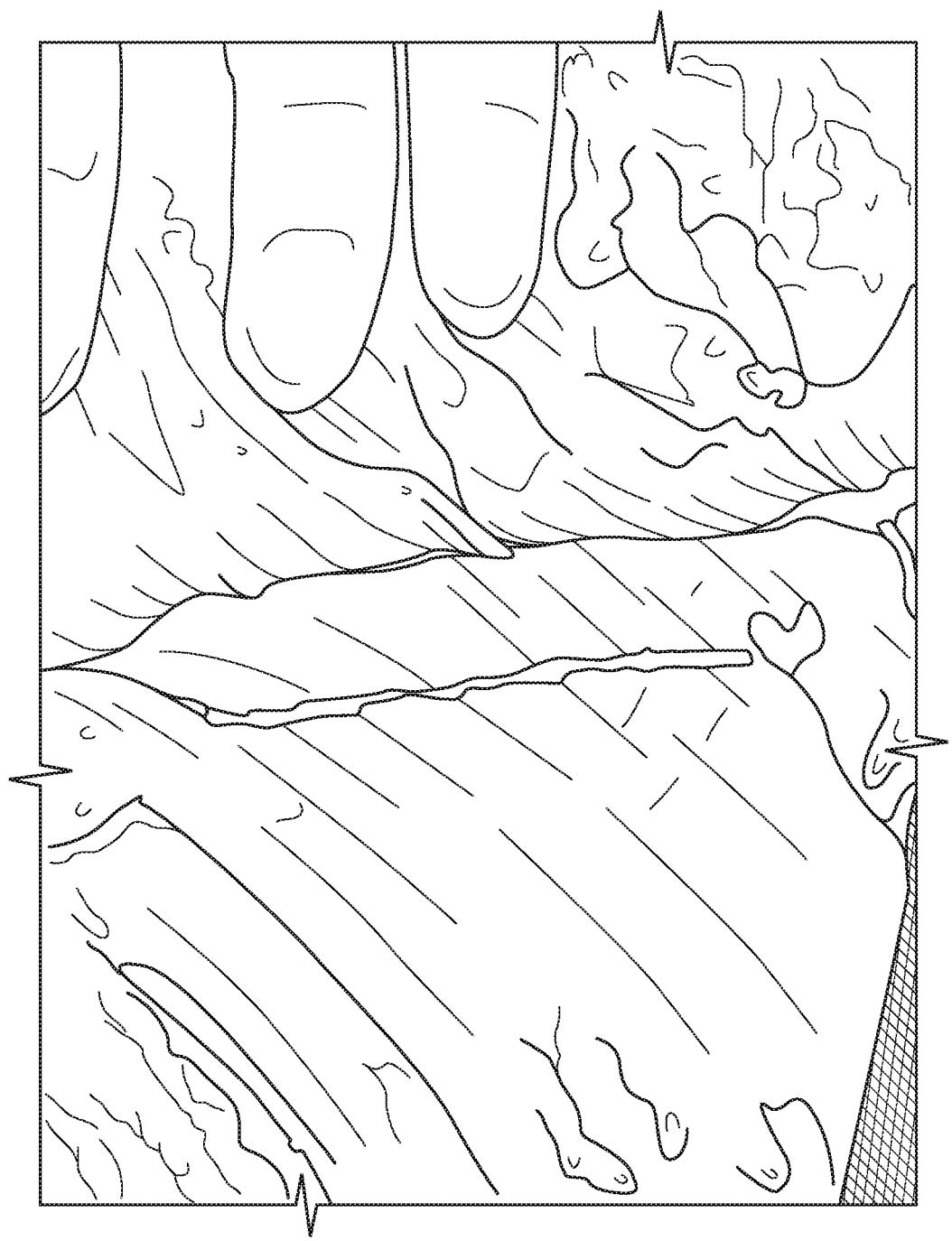
FIG. 2B shows intraoperative DIEP flap dissection with emphasis at the lateral raw perforators and lateral rectus border.
Figure 3A:
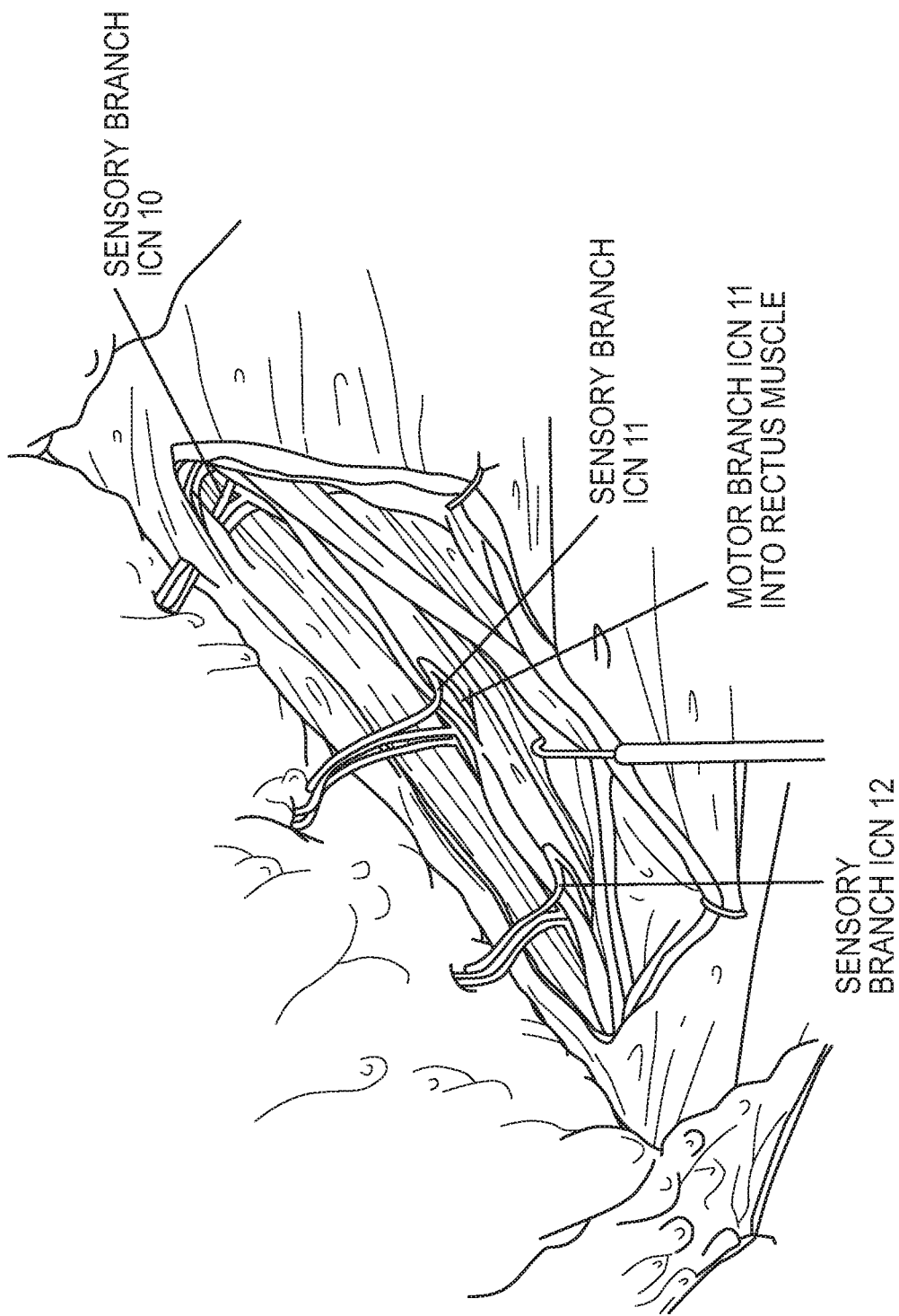
FIG. 3A shows exposure of the ICNs after the incision of anterior rectus sheath and longitudinal rectus muscle fibers spread. Schematic representation of the retrograde dissection of sensory component of the intercostal nerves (yellow) until joining the motor components (green) at an intramuscular sensory-motor Y junction. If medial row perforators were dominant and used for flap supply, lateral anterior rectus sheet fascial opening and rectus spread might be limited only to allow sensory ICN harvest.
Figure 3B:
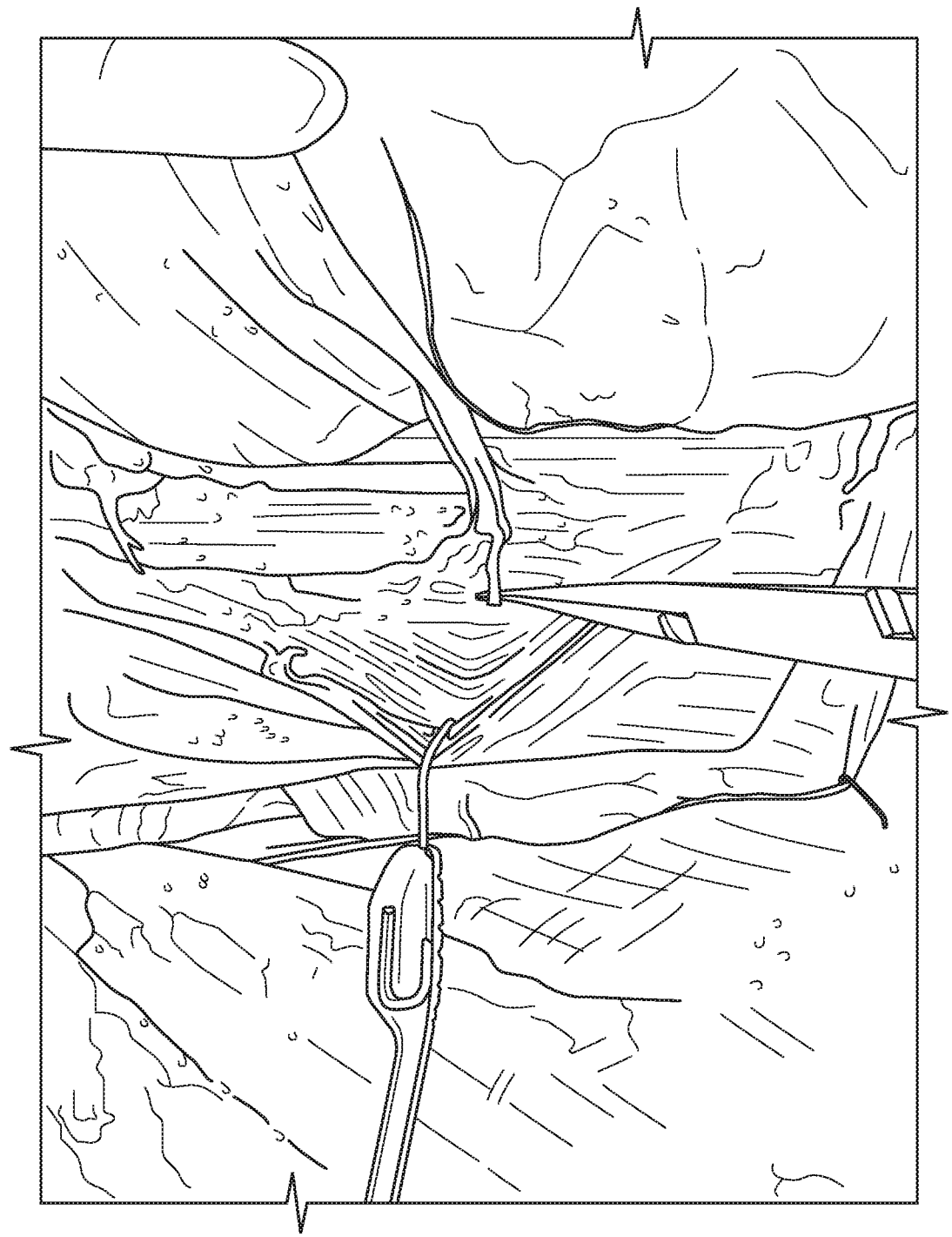
FIG. 3B shows intraoperative view of a dissected sensory ICN component as marked by the tip of the forceps.

Preoperative markings were made with the patient standing. The patient is subsequently brought to the operating room and placed in supine position with bilateral arms abducted. The abdominal flap (FIG. 1) is dissected in a standard lateral to medial fashion until lateral row perforators and associated intercostal nerves are exposed (FIGS. 2A-2B). The anterior rectus sheath is incised craniocaudally along the lateral row perforators to expose the rectus abdominis muscle, lateral perforator vessels, and intercostal nerves (ICN) 11 and ICN12 (FIGS. 3A-3B).

Upon identification of ICN11 and/or ICN12, next to the lateral row of vascular perforators, standard retrograde dissection of the sensory branch of the intercostal nerve ICN11 and/or ICN12 is traced until a sensory-motor Y-junction is encountered. While this may be seen intra- or retro-muscularly, the exposure can be accomplished by longitudinal spread rather than transection of the rectus muscle fibers, thus preserving its integrity.

Care must be exercised to protect the lateral row vascular perforators in the case these are planned to be incorporated into a DIEP flap. However, with this technique if the medial row vascular perforators are used as a dominant vascular supply to the flap, vertical anterior rectus fascial split along lateral perforators and rectus muscle spread might be minimized and limited to only allow ICN sensory graft harvest, without extensive fascial opening or dissection.

Figure 4A:
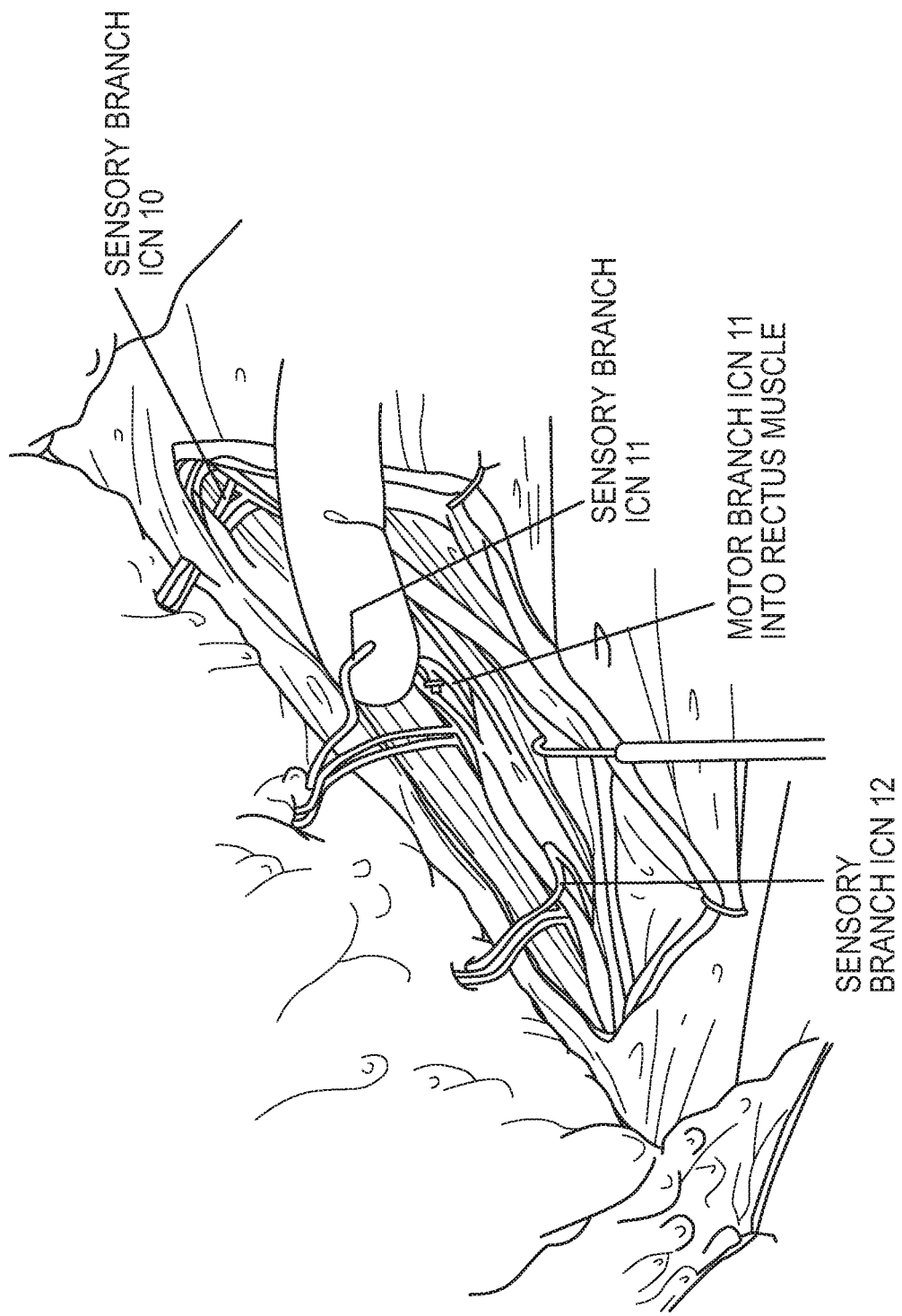
FIG. 4A shows separation of sensory component of ICN11, just distal to Y-junction with preserved motor component. Schematic showing resulting sensory nerve pedicle (yellow) and preserved motor component (green) with longitudinally dissected rectus muscle.
Figure 4B:
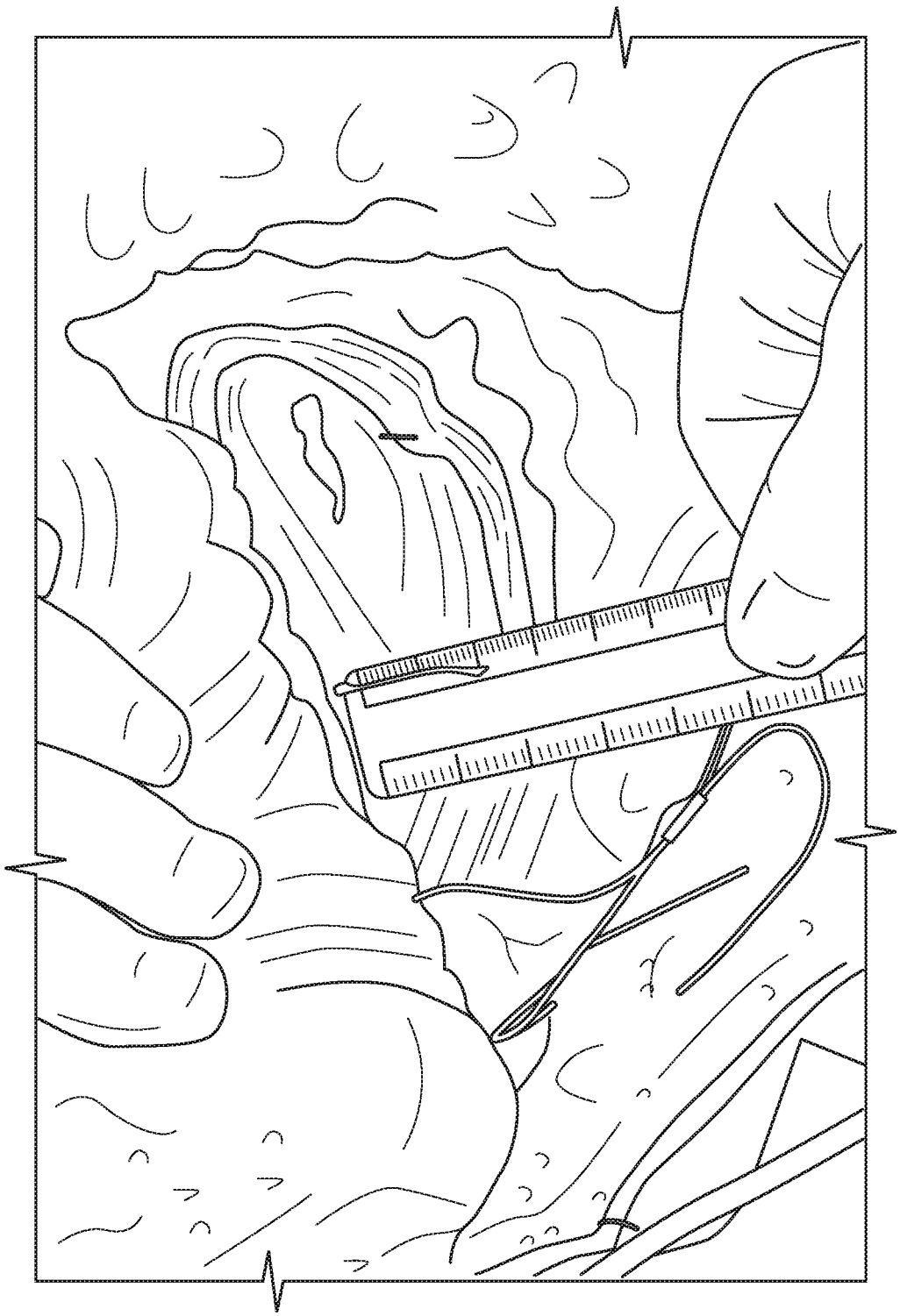
FIG. 4B shows intraoperative picture showing resultant sensory nerve pedicle to be used for neurotization.

In addition to the retrograde dissection of sensory ICN11 and/or ICN12 branch, the motor component is preserved to prevent denervation of the rectus abdominis muscle. The motor preservation is performed even when the lateral perforators are chosen as the dominant vascular supply. This is accomplished by harvesting the sensory component just distal to the sensory-motor Y-junction, leaving the motor innervation to the lateral rectus abdominis muscle intact (FIGS. 4A-B).

The inclusion of one or two ICNs depends on whether a single or dual innervation of the flap is desired. Once sensory ICN branch(es) are dissected and divided, the remainder of the DIEP flap vascular dissection is completed, leaving the flap perfused until chest dissection is complete.

Figure 5:
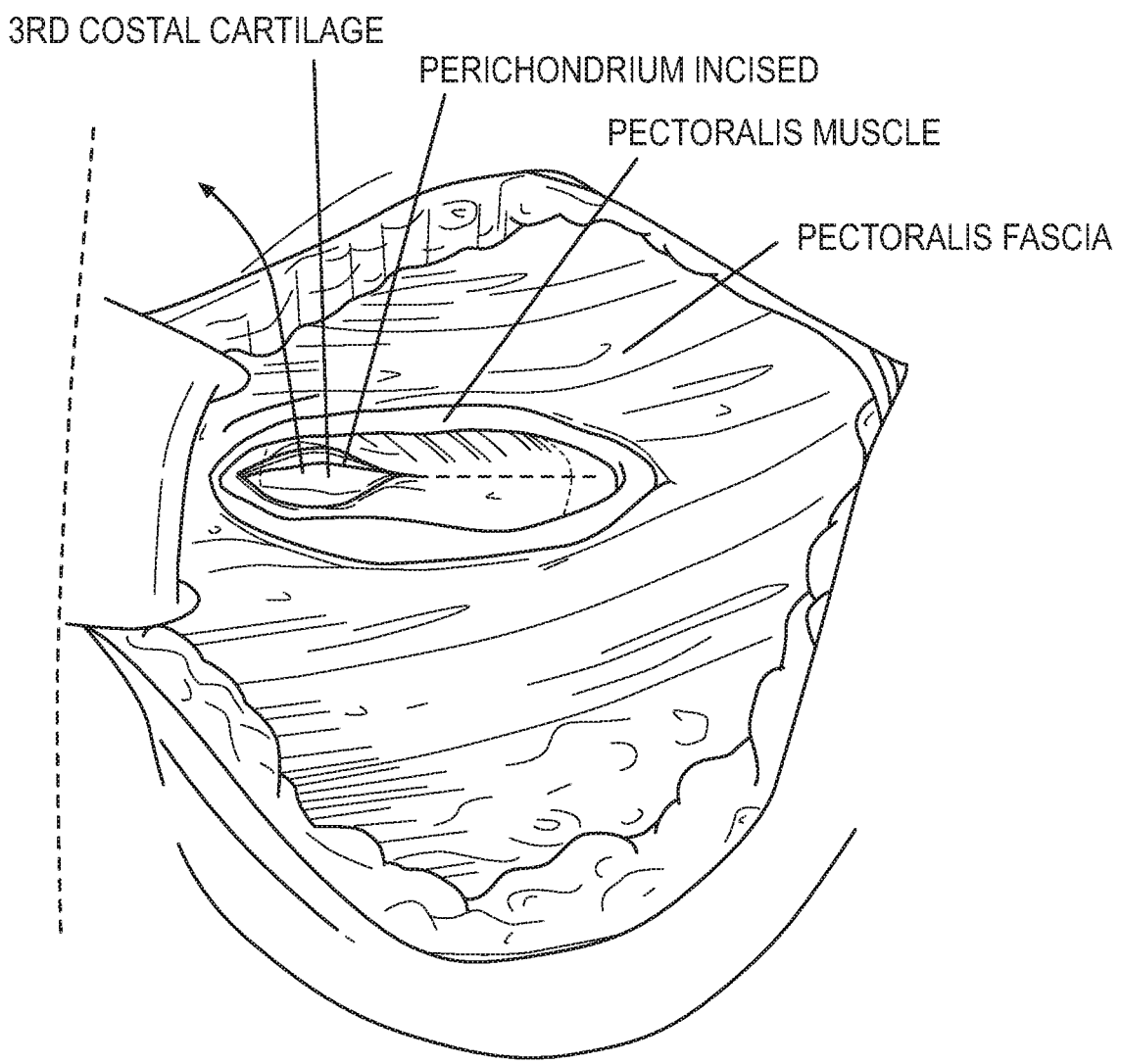
FIG. 5 shows dissection approach to third rib cartilage. Schematic showing the resulting defect following mastectomy, pectoralis major muscle is longitudinally spread and the perichondrium is incised and separated circumferentially, in preparation for the third rib cartilage for removal. Dashed vertical line is sternum.

Following mastectomy, the pectoralis major muscle fibers are longitudinally split over the third costal cartilage to expose the perichondrium of the third rib. The perichondrium is incised and subperichondrial dissection performed, followed by the removal of the third costal cartilage. Next, the posterior perichondrium is carefully incised and a lateral-to-medial dissection is performed until the internal mammary vessels are visualized (FIG. 5).

Figure 6A:
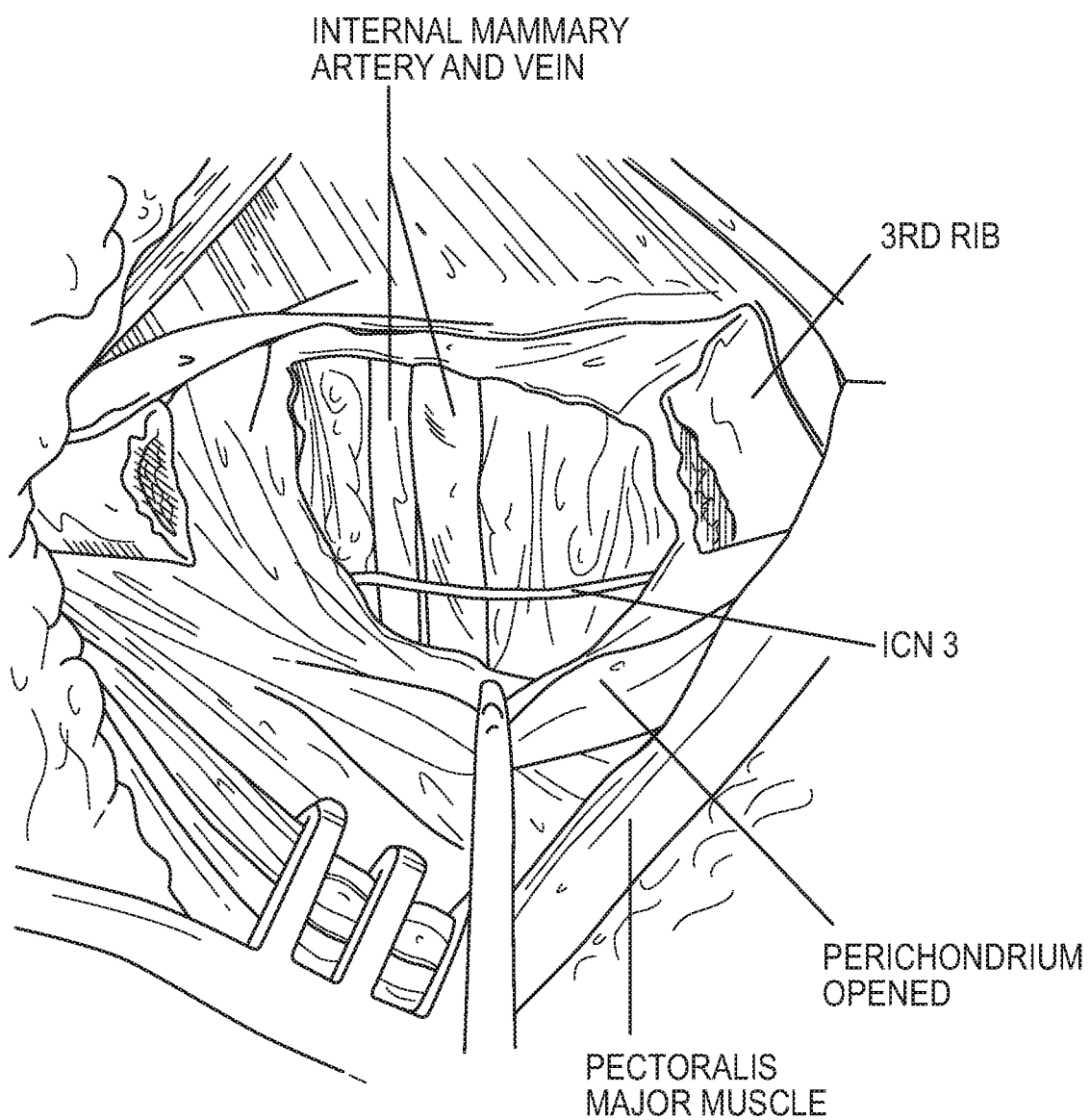
FIG. 6A shows schematic drawing showing internal mammary artery and vein after removal of the cartilage. ICN3 is available for use after careful separation from third rib cartilage and perichondrium.
Figure 6B:
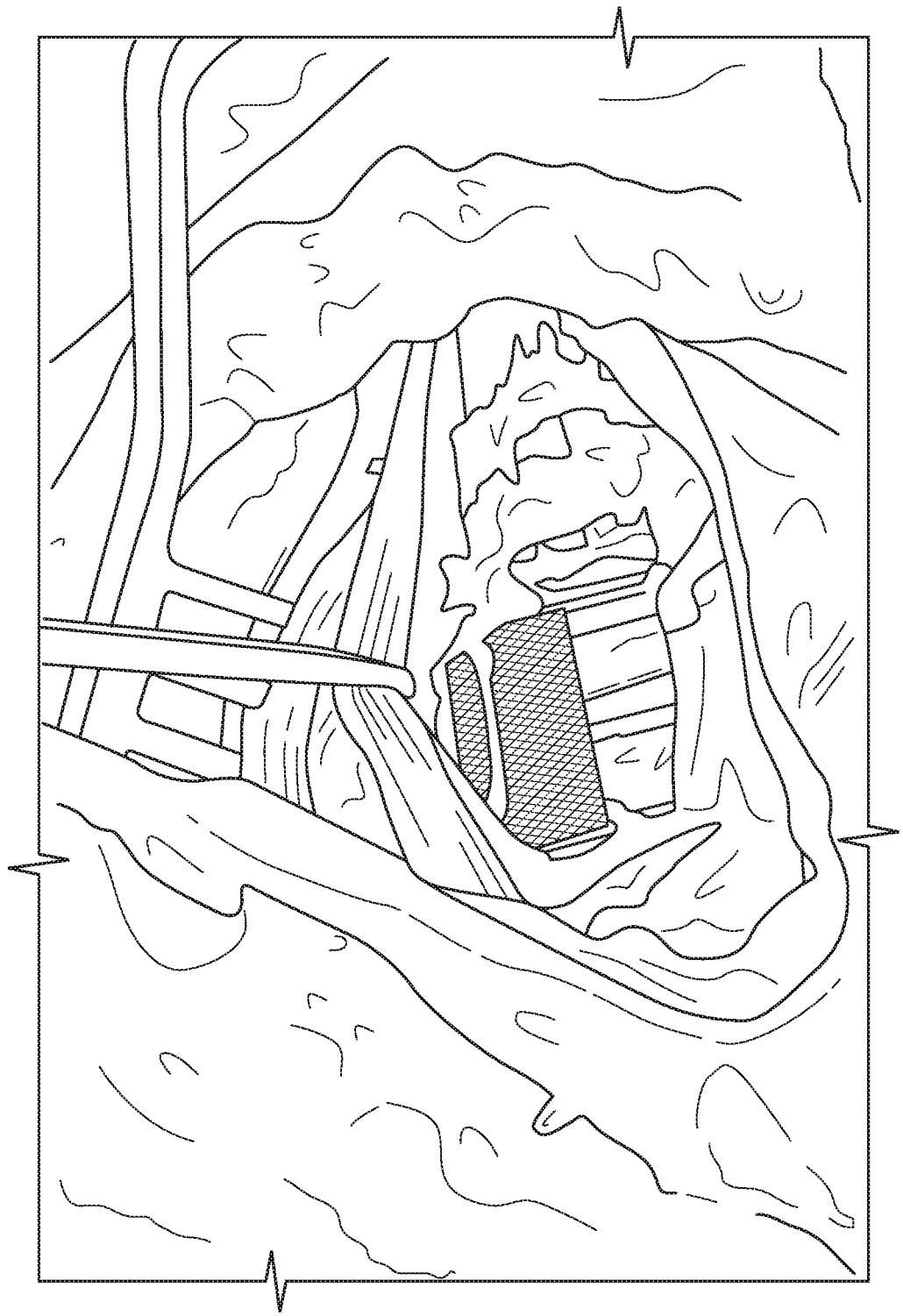
FIG. 6B shows anatomical specimen dissection identifying ICN3 in its location along the inferior third rib cartilage.
Figure 6C:
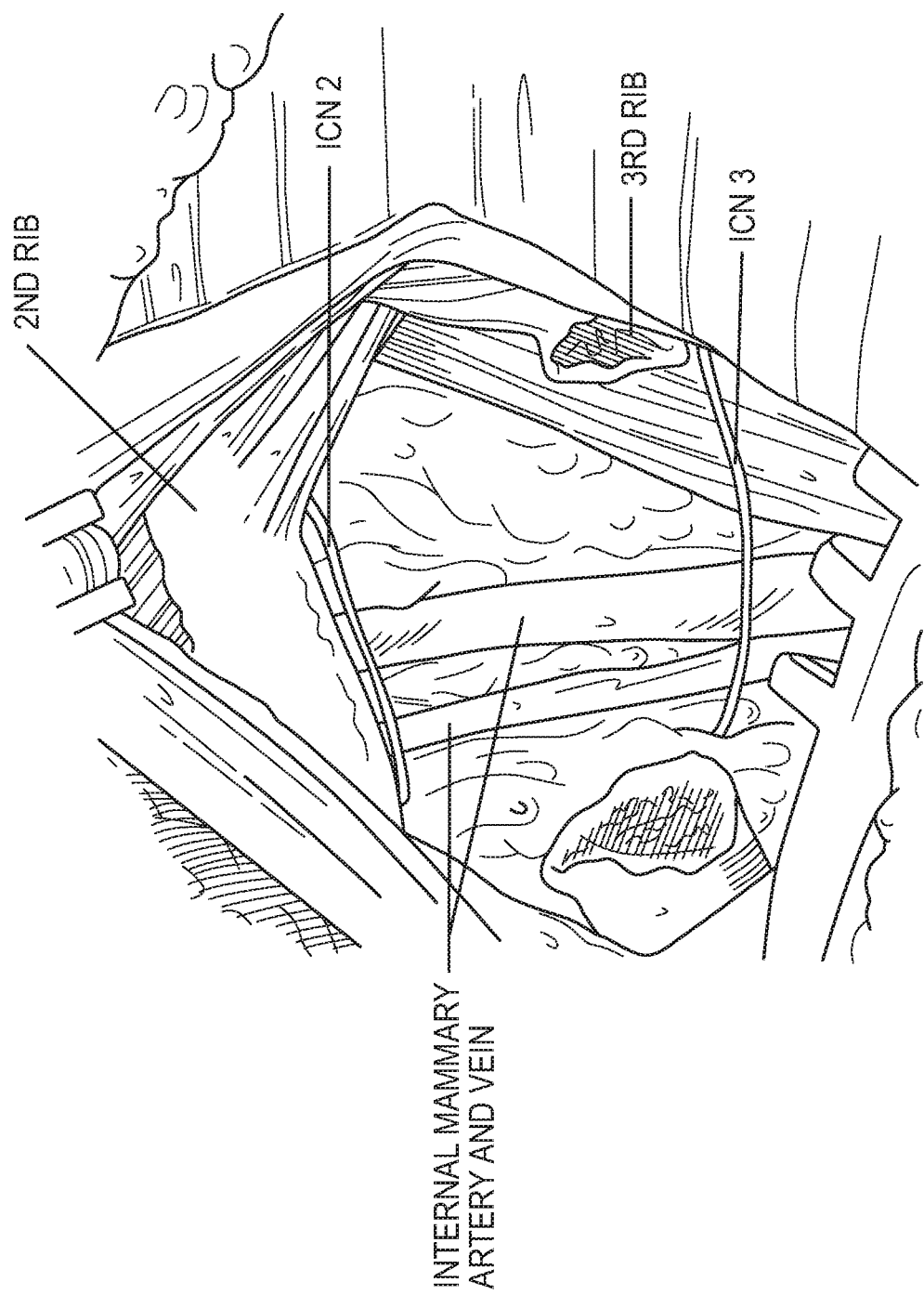
FIG. 6C shows schematic showing ICN2 exposed by careful dissection from perichondrium and the inferior border of second rib cartilage if dual innervation with ICN3 is desired.
Figure 6D:
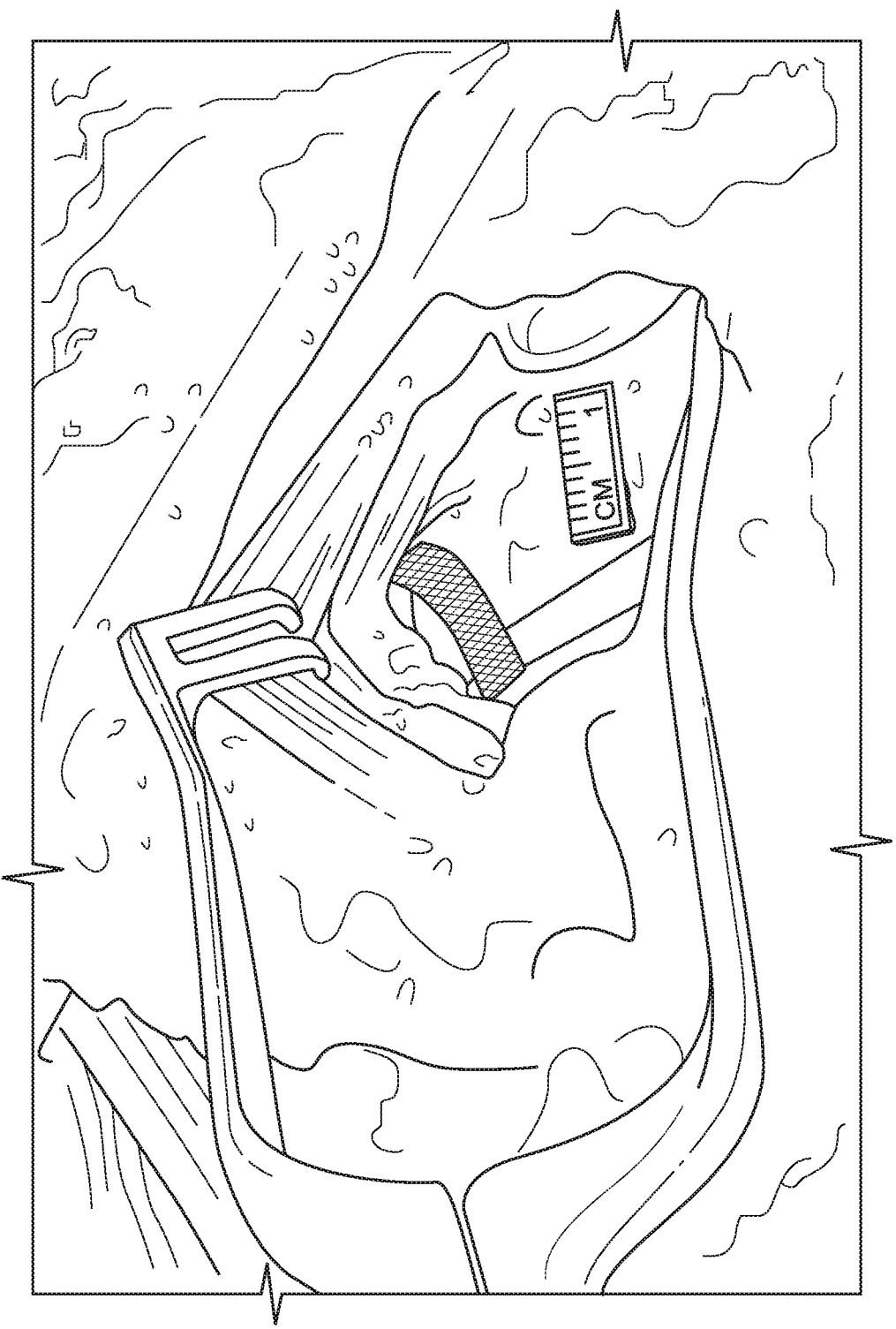
FIG. 6D shows specimen dissection identifying ICN2 in its location.

It is important to recognize that the ICN3 runs along the inferior border of third rib (FIGS. 6A-6B). Once identified under the perichondrium and along the inferior rib border, it is preserved, traced medially, then divided, and reflected laterally for subsequent nerve coaptation. If dual innervation is desired, then the ICN2 can be found within the upper pole of the surgical field, under the perichondrium, just inferior to and along the second rib border (FIGS. 6C-6D).

Figure 7A:
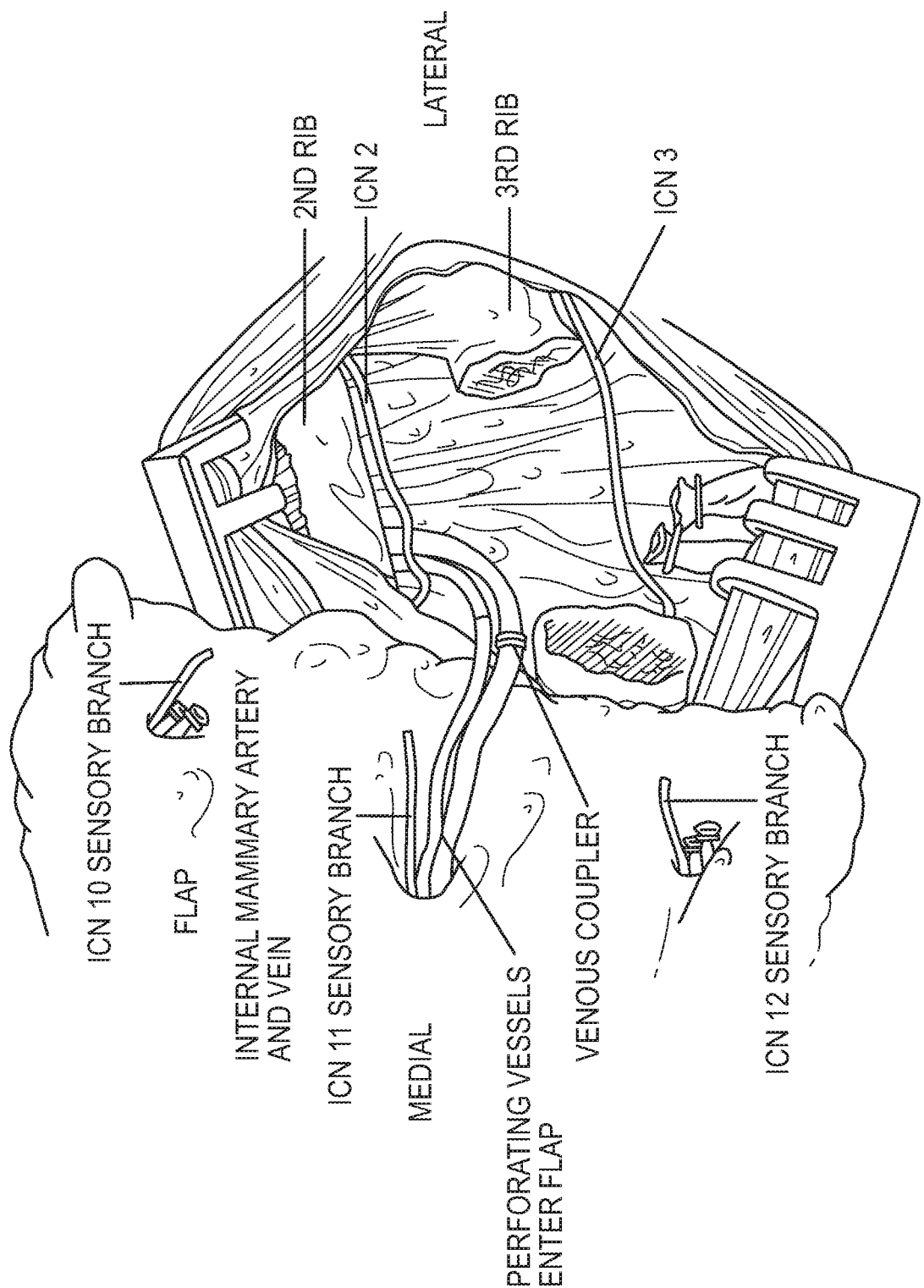
FIG. 7A shows vascular anastomosis of flap DIEA/DIEV to internal mammary artery and vein. 7A. Schematic showing internal mammary artery and vein are dissected and separated inferiorly, which was then anastomosed to the DIEP flap perforators. Yellow marked flap available donor nerves are sensory ICN11 and ICN12, while recipient chest nerves are INC2 and ICN3.
Figure 7B:
FIG. 7B shows intraoperative view of connected flap and chest vessels, and dissected ICN3 in preparation for nerve reconstruction.
Figure 8A:
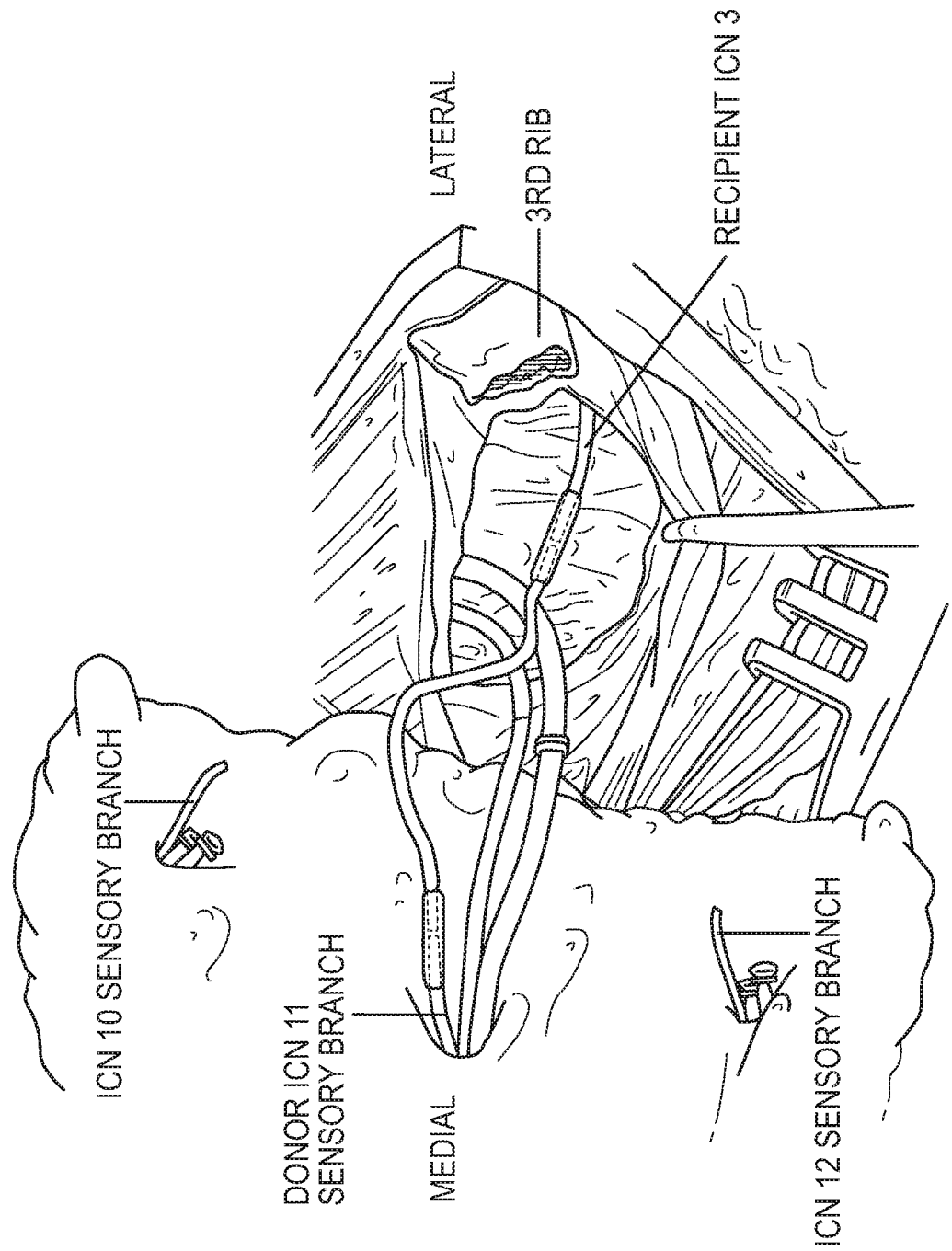
FIG. 8A shows bridging of donor nerves to recipient nerves with processed human nerve allograft. Schematic showing tension free single nerve neurotization with ICN11 and ICN3 with coaptation of the nerve facilitated by translucent porcine intestinal submucosa nerve connector, as alternative to direct suture.
Figure 8B:
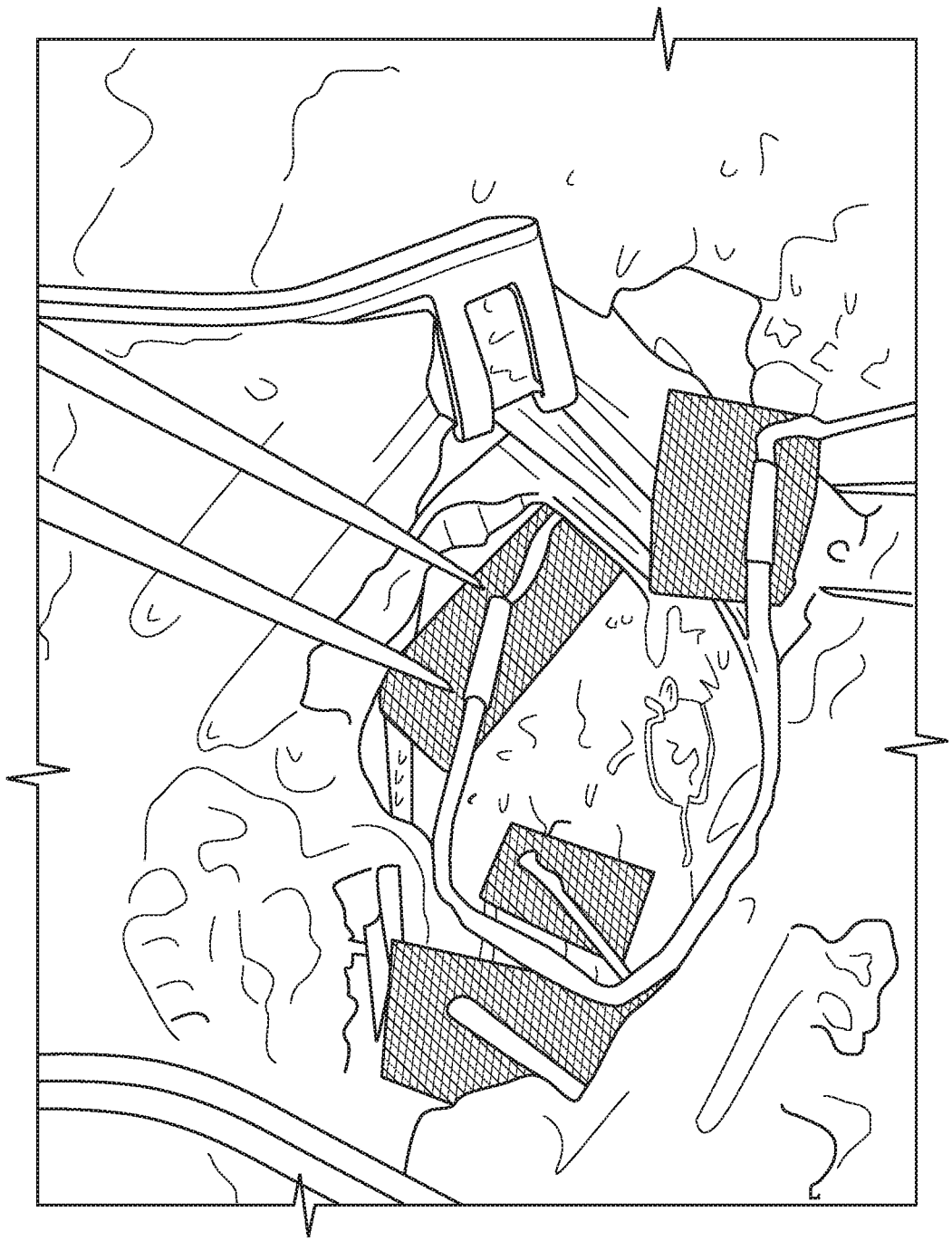
FIG. 8B shows specimen illustration of single nerve breast neurotization.
Figure 8C:
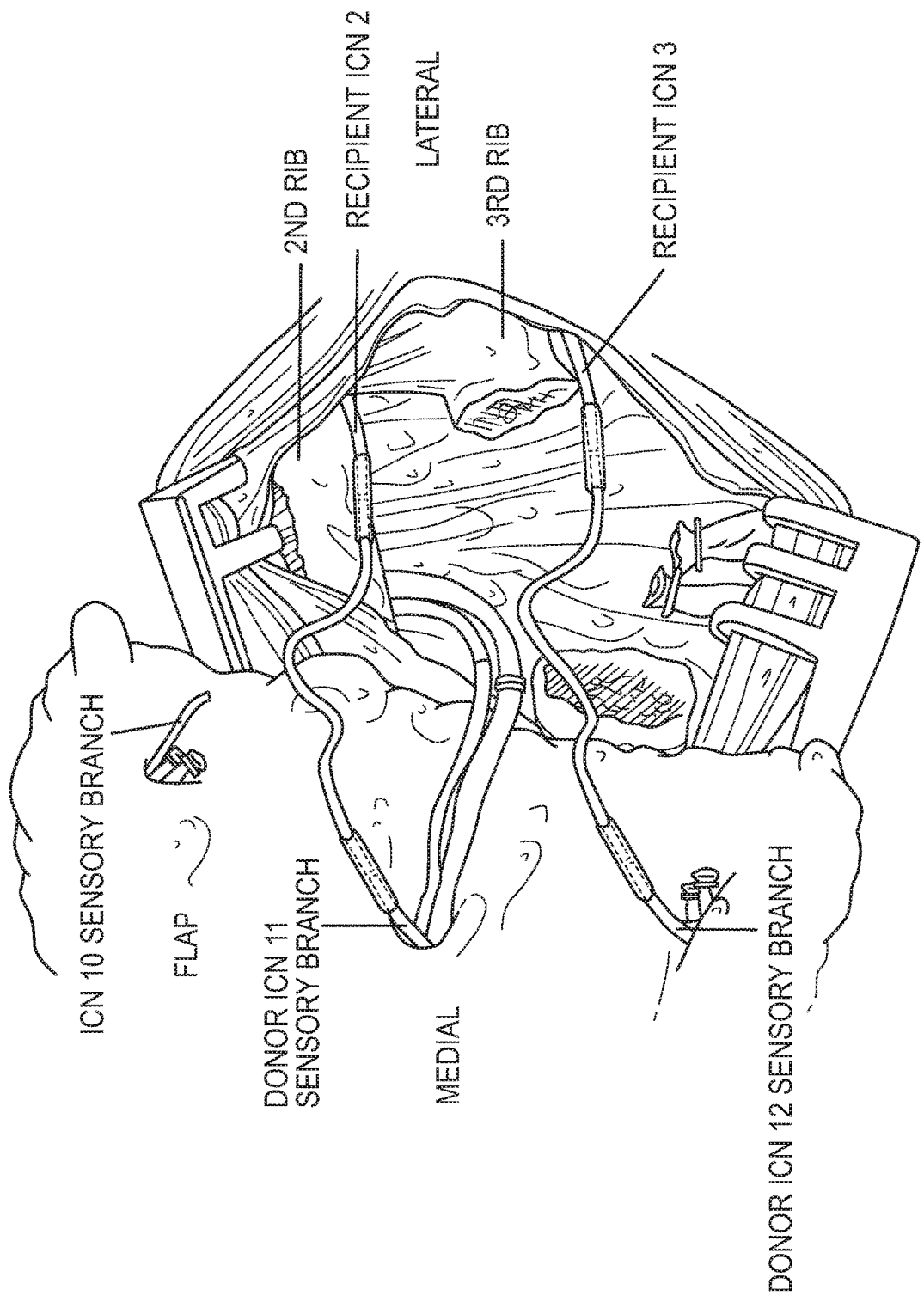
FIG. 8C shows schematic showing tension free dual nerve neurotization with ICN11 and ICN12 connected to ICN2 and ICN3, respectively.
Figure 8D:
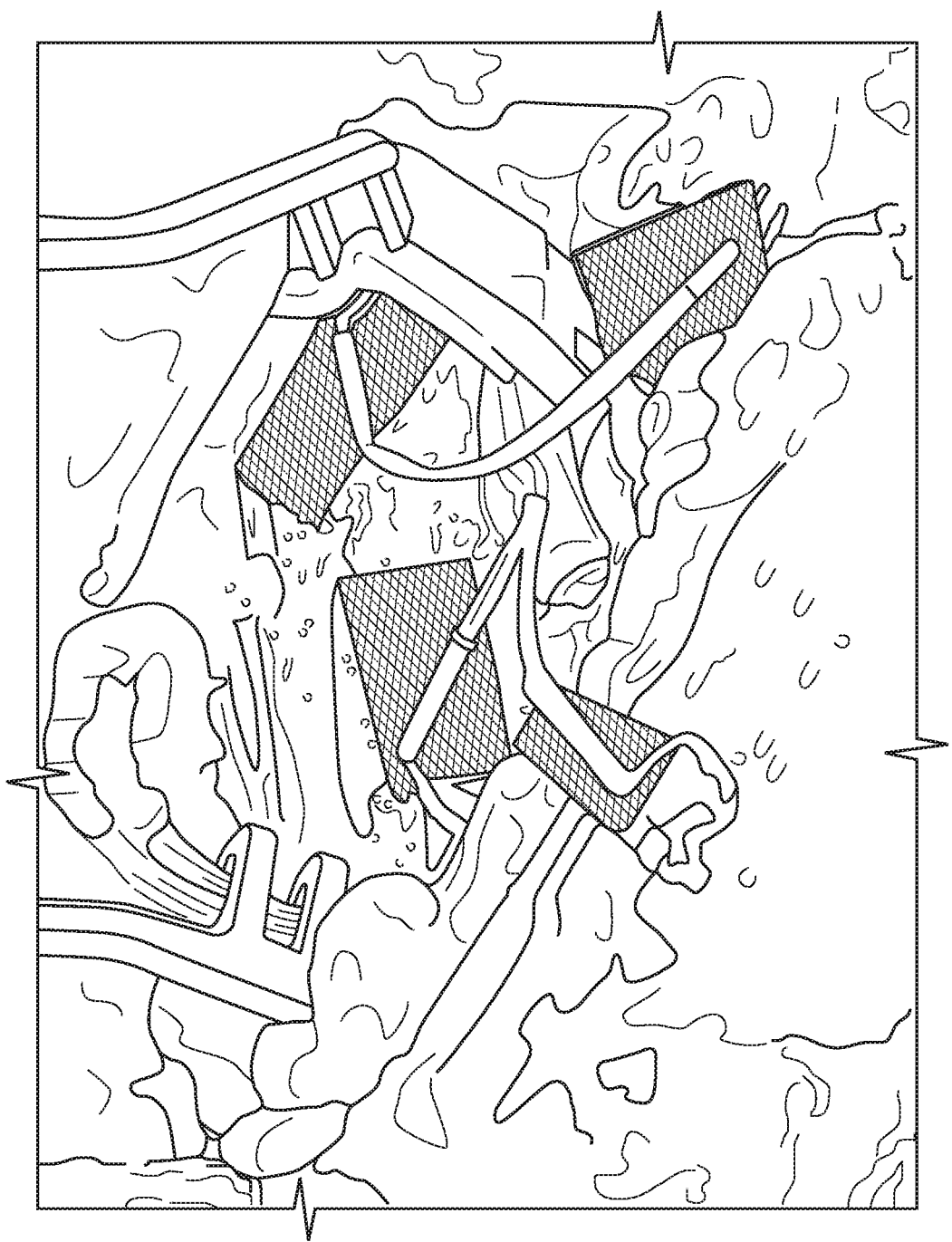
FIG. 8D shows specimen illustration of dual nerve breast neurotization.

The flap is then disconnected from the donor-site and brought to the chest. Microsurgical arterial and venous anastomosis is performed in standard fashion (FIGS. 7A-7B). To preserve the flap's full arch of rotation required to inset the flap, and to ensure tension-free nerve repair, the nerve coaptation is performed using a 1-2 mm×50 or 1-2 mm×70 processed human nerve allograft (Avance® Nerve Graft, AxoGen, Alachua Fla.) to bridge the gap. The interposing nerve allograft is then microsurgically connected to chest recipient and flap donor nerve ends via direct suture, alternatively, proximal and distal coaptation can be facilitated with a translucent and porous porcine intestinal submucosa nerve connector (AxoGuard Nerve Connector, AxoGen, Alachua Fla.) (FIG. 8A,B). The flap is then inset and the abdominal donor site closed in standard fashion, thus, completing the neurotized DIEP flap breast reconstruction.

Example 2—Advantages Provided by the Surgical Methods of the Invention

Homogeneity of a surgical approach is critical to reliably comment on the efficacy of a procedure or a procedural concept such as breast neurotization. Hence, establishing a standardized surgical technique is important to facilitate future homogenous comparative analysis. A clear understanding of the principles of nerve surgery as well as expertise regarding the characteristics of available reconstructive choices like nerve conduits, autografts, and processed nerve allografts are critical for successful execution of this proposed procedure.

Standard treatment of nerve injuries consists of tensionless primary repair whenever possible. However, if primary repair is not possible, then bridging materials are utilized, which include nerve autografts, tube conduits, and processed nerve allografts. The nerve gap encountered with breast neurotization typically measures between 50 to 70 mm, thus, far exceeding the length that is recommended for reconstruction with nerve conduits. While nerve autografts have traditionally been preferred when reconstructing extremity nerve defects, they are associated with donor-site complications including additional incisions, wound healing issues, painful neuroma formation, or bulge/incisional hernias if rectus muscle is denervated.

By using a processed nerve allograft, donor-site complications associated with the harvest of nerve autografts can be avoided. Processed nerve allograft is an extracellular matrix (ECM) scaffolding created from donated human peripheral nerve tissue that has been decellularized, pre-degenerated, and sterilized, which results in a cell-free microstructural architecture with the protein composition of nerve tissue. The decellularization of the allograft significantly reduces the risk of immune rejection issues, thus eliminating the need for immunosuppressive therapy. The resultant allograft is composed of bundles of endoneurial microtubes, contained within the original nerve's fascicle and epineurial scaffold, which is comprised of ECM proteins (laminin, fibronectin, and glycosaminoglycans) that provide natural axonal growth cues for guided regrowth, otherwise not found in hollow tube conduits.

The first critical element of the donor site dissection depends on identification and perseveration of the donor intercostal nerves. Cadaveric studies have found that the rectus abdominis is innervated by nerves from the rectus sheath plexus that run parallel with the most lateral branch of the DIEA before running with arterial perforators into the rectus abdominis and anterior abdominal wall. Thus, the lateral branch of the DIEA and lateral row perforators are intimately related to the intercostal nerves that innervate the rectus abdominis muscle and any damage incurred to these structures during DIEP flap harvest would contribute to the previously mentioned donor-site morbidity of abdominal wall weakness, abdominal bulge, or hernia. Although DIEP flap aims to overcome TRAM (transversus rectus abdominis muscle) flap shortcomings, the reported incidence of abdominal bulge or incisional hernia occurrence after a DIEP flap is still 3-5%. By conserving the motor component of the lateral intercostal nerves to the lateral rectus, abdominal wall morbidity should be minimized even further.

Figure 9A:
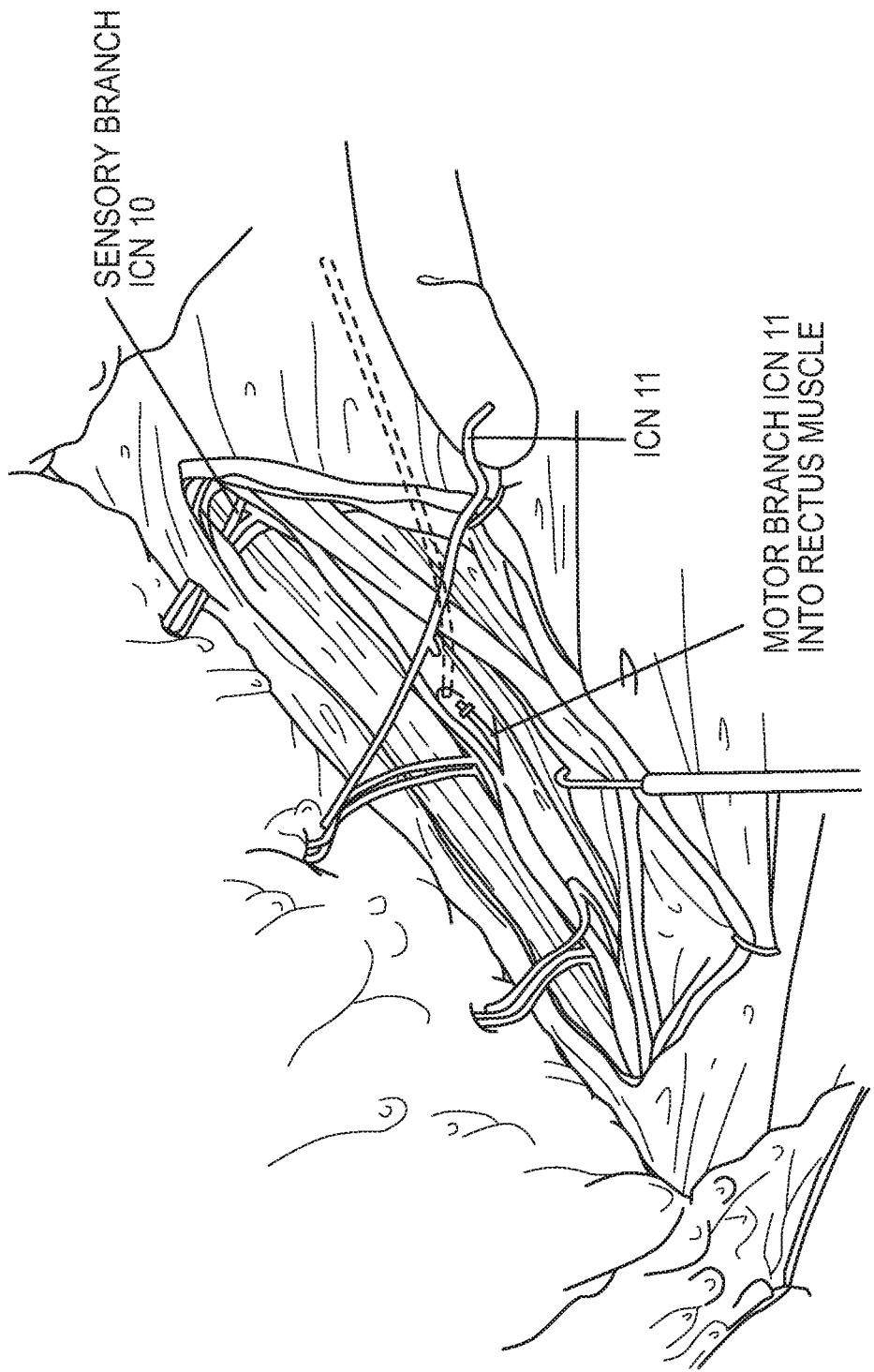
FIG. 9A shows traditional dissection and separation of donor intercostal nerve. Schematic showing the donor pedicle that consists of both sensory (yellow) and motor (green) components that were dissected out of the rectus abdominis muscle (original position of pedicle illustrated by dashed yellow line).
Figure 9B:
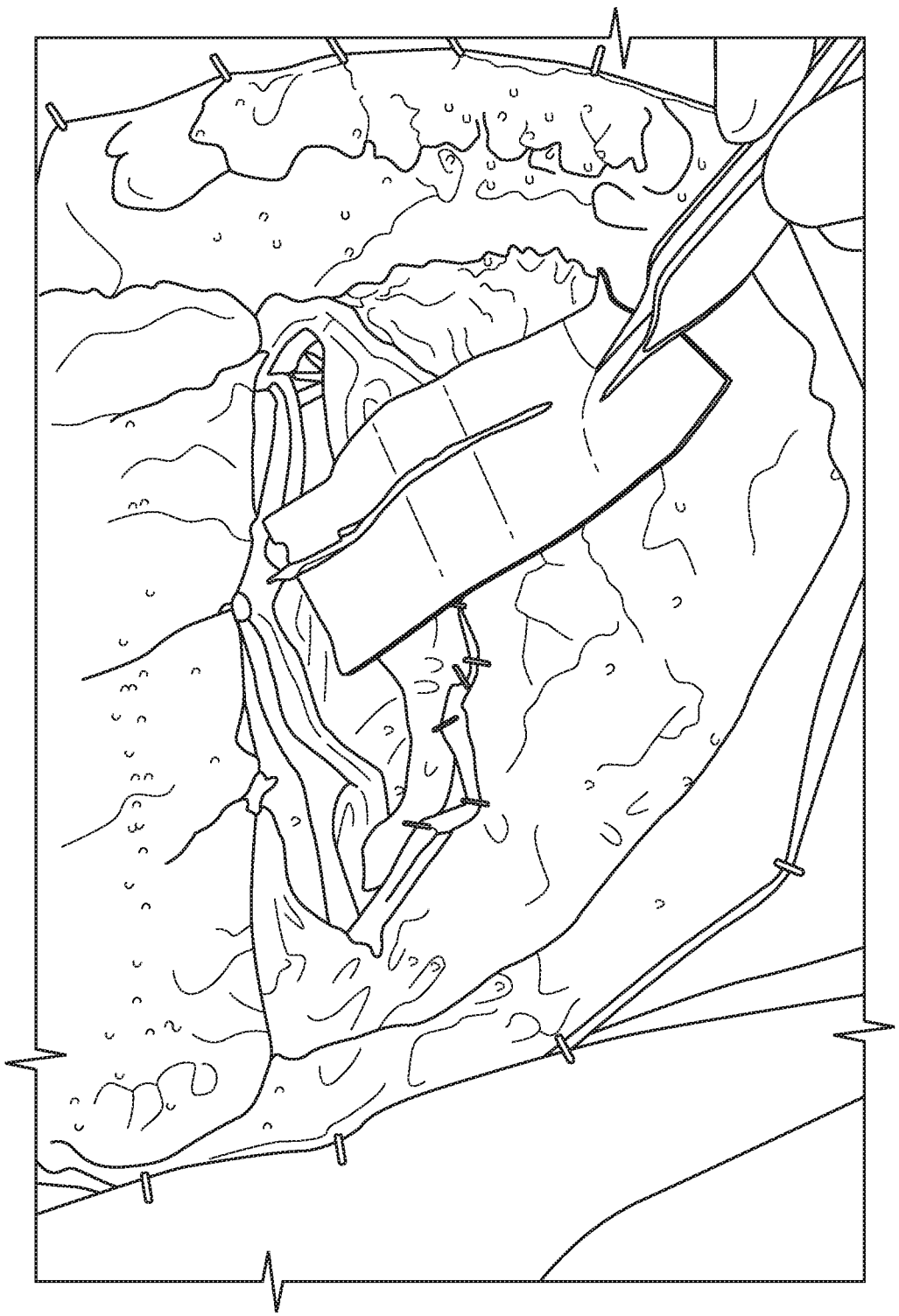
FIG. 9B shows intraoperative picture of traditional dissection of donor intercostal nerve that contains both sensory and motor components.

An equally important element of the donor site dissection is the methodology by which the sensory nerves are exposed and harvested. Routinely, the motor branch is often sacrificed and taken in conjunction with the sensory component during the flap dissection and/or autograft harvest. This approach elongates the extracted nerve by approximately 10-12 cm in length, but in addition to risking rectus abdominis denervation there is another common overlooked risk in utilizing a combined sensorimotor nerve (FIGS. 9A-9B). The risk is that as the recipient nerve begins to regenerate distally and joins with the donor nerve, the sensory branch may regenerate into the clipped motor component with only up to 50% of fibers feeding the sensory branch. This is expected to decrease the degree of sensory recovery. To address this risk, using only the sensory components of ICN11 and/or ICN12 is proposed. To extract only the sensory component while preserving the motor branches, the cutaneous sensory nerves will be followed proximally in a retrograde fashion to the Y-junction where it joins the motor component before continuing proximally as a mixed nerve. The sensory component is harvested at the Y-junction, fully preserving the motor branches going into the lateral rectus abdominis. The pure sensory nerve pedicle is relatively short and therefore, a processed nerve allograft can be used if necessary to bridge the gap (FIG. 8). This approach is suggested to provide a proper anatomical platform aiming to optimize the chances of neurotization and meaningful recovery, while also fully preserving rectus abdominis innervation.

Also equally important are the critical elements at the recipient site, which depend on the careful dissection and identification of ICN2 and/or ICN3. ICN3 is the recipient nerve of choice, but ICN2 can also be reliably found in the anterior chest within the same surgical field.

The processed nerve allograft overcomes the short nerve pedicle from the DIEP flap and allows for a tension-free nerve coaptation. Alternatively, if the thoracodorsal vascular system is chosen as the vascular supply, then the lateral ICN4 can be used along the anterior axillary line.

Otherwise ICN4 can be used with the internal mammary vascular system, because there are two pivoting points, one vascular medially, and the other nerve laterally, which might affect the extent of flap rotation and inset. In addition, erogenous nipple/areola sensory innervation is primarily carried by the lateral branches of ICN4 and the implications of using a nerve with these functions for breast neurotization at this time is not well understood.

Thus, if ICN4 is used to neurotize the entire breast flap, then there may be sequelae related to overstimulation. Taking this into consideration, as well as the fact that lateral branches of ICN4 are usually transected at the level of the chest wall musculature in the process of mastectomy, these branches are mostly unavailable for neurotization, unless specifically dissected and preserved before or during the mastectomy.

Due to aforementioned concerns related to ICN4, ICN4 may not be preferred as a dominant recipient for breast neurotization.

Lastly, as an alternative to standard direct suture allograft-nerve coaptation, connector-assisted microsurgical coaptation of the interposing nerve allograft between the flap donor and chest recipient nerves, may facilitate growth across the coaptation site without fascicular misalignment or undue axonal escape.

The surgical methods of the invention revolutionize breast reconstruction by offering a reliable, reproducible, and effective neurotization procedure.

I claim:

1. A set of nerve grafts to be used in neurotization of a breast of a subject, the set of nerve grafts comprising:
   at least two nerve grafts, wherein the at least two nerve grafts comprise processed segments of harvested intercostal nerves (ICNs) obtained from one or more animal sources,
   wherein a first nerve graft of the at least two nerve grafts is a processed segment of a sensory component, and not a motor component, of a first ICN, and wherein a second nerve graft of the at least two nerve grafts is a processed segment of a sensory component, and not a motor component, of a second ICN, wherein the first ICN and the second ICN are differently numbered ICN, and wherein the set of nerve grafts is configured to bridge a nerve gap having a length of 50 mm to 70 mm.

2. The set of nerve grafts of claim 1, wherein the first nerve graft and the second nerve graft are obtained from a single animal source.

3. The set of nerve grafts of claim 1, wherein the first nerve graft and the second nerve graft are obtained from different animal sources.

4. The set of nerve grafts of claim 1, wherein the first nerve graft and the second nerve graft are obtained from a ruminant.

5. The set of nerve grafts of claim 4, wherein the ruminant is a sheep, a cow, a horse, a pig, or a goat.

6. The set of nerve grafts of claim 1, wherein at least one of the first nerve graft or the second nerve graft is configured for implantation relative to a third ICN, and wherein the third ICN is a differently numbered ICN than the first ICN and the second ICN.

7. The set of nerve grafts of claim 1, wherein at least one of the first nerve graft or the second nerve graft is configured for implantation in a sensory portion of a third ICN associated with the breast for use in neurotization of the breast of the subject.

8. The set of nerve grafts of claim 1, wherein each of the at least two nerve grafts is 50 mm or 70 mm in length.

9. A set of nerve grafts comprising:
at least two nerve grafts obtained from one or more animal sources, wherein the at least two nerve grafts comprise processed segments of one or more harvested intercostal nerves (ICNs), which include sensory components, and not motor components, of the one or more ICNs, and wherein the set of nerve grafts is configured to bridge a nerve gap having a length of 50 mm to 70 mm.

10. The set of nerve grafts of claim 9, wherein the one or more ICNs include at least two differently numbered ICNs.

11. The set of nerve grafts of claim 9, wherein the one or more ICNs are obtained from a ruminant.

12. The set of nerve grafts of claim 11, wherein the ruminant is a sheep, a cow, a horse, a pig, or a goat.

13. The set of nerve grafts of claim 9, wherein the at least two nerve grafts are configured for use in neurotization of a breast of a subject.

14. The set of nerve grafts of claim 9, wherein each of the at least two nerve grafts is 50 mm or 70 mm in length.

15. A surgical method for breast neurotization, the method comprising:
implanting at least two nerve grafts into a subject to bridge a nerve gap having a length of 50 mm to 70 mm, wherein the at least two nerve grafts comprise processed segments of one or more ICNs harvested from one or more animal sources, and wherein the segments of the one or more ICNs include sensory components, and not motor components, of the one or more ICNs.

16. A method of preparing a set of nerve grafts for breast neurotization, the method comprising:
harvesting at least two intercostal nerves (ICNs) from one or more animal sources; and
processing the at least two ICNs to form the set of nerve grafts, wherein the set of nerve grafts is configured to bridge a nerve gap having a length of 50 mm to 70 mm and wherein the segments of the one or more ICNs include sensory components, and not motor components, of the one or more ICNs.

17. The method of claim 16, wherein a length of each of the at least two nerve grafts is 50 mm or 70 mm.

18. The method of claim 16, wherein a first nerve graft of the at least two nerve grafts is a processed segment of a first ICN, and wherein a second nerve graft of the at least two nerve grafts is a processed segment of a second ICN, wherein the first ICN and the second ICN are differently numbered ICNs.

19. The method of claim 16, wherein a first nerve graft and a second nerve graft, of the at least two nerve grafts, are processed segments of the same number ICN.

* * * * *

UNITED STATES PATENT AND TRADEMARK OFFICE
CERTIFICATE OF CORRECTION

PATENT NO. : 11,147,558 B2
APPLICATION NO. : 16/192261
DATED : October 19, 2021
INVENTOR(S) : Ducic Page 1 of 1

It is certified that error appears in the above-identified patent and that said Letters Patent is hereby corrected as shown below:

In the Claims

Column 10, Line 47, in Claim 1, delete the third instance of "ICN" and insert --ICNs--.
Column 12, Line 12, in Claim 16, delete "70 mm" and insert --70 mm,--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*